US012685559B2

(12) United States Patent
Breton et al.

(10) Patent No.: US 12,685,559 B2
(45) Date of Patent: Jul. 21, 2026

(54) DRIVE ASSEMBLY FOR SURGICAL ROBOTIC SYSTEM

(71) Applicant: Vicarious Surgical Inc., Waltham, MA (US)

(72) Inventors: Alexander Breton, Cambridge, MA (US); Allison M. Stauffer, Cambridge, MA (US); Maeve Devlin, East Boston, MA (US); Eric Kline, Malden, MA (US); Sammy Khalifa, Medford, MA (US)

(73) Assignee: Vicarious Surgical Inc., Waltham, MA (US)

( * ) Notice: Subject to any disclaimer, the term of this patent is extended or adjusted under 35 U.S.C. 154(b) by 478 days.

(21) Appl. No.: 18/114,928

(22) Filed: Feb. 27, 2023

(65) Prior Publication Data

US 2023/0270321 A1     Aug. 31, 2023

Related U.S. Application Data

(60) Provisional application No. 63/314,090, filed on Feb. 25, 2022.

(51) Int. Cl.
A61B 17/34 (2006.01)
A61B 34/30 (2016.01)
(Continued)

(52) U.S. Cl.
CPC .............. A61B 17/34 (2013.01); A61B 34/30 (2016.02); B25J 9/126 (2013.01); H02K 7/14 (2013.01); *A61B 2034/302* (2016.02)

(58) Field of Classification Search
CPC ... A61B 17/34; A61B 34/30; A61B 2034/302; B25J 9/126; H02K 7/14
(Continued)

(56) References Cited

U.S. PATENT DOCUMENTS 10,285,765 B2     5/2019   Sachs et al.
10,603,126 B2     3/2020   Karguth et al.
(Continued)

FOREIGN PATENT DOCUMENTS

CN        103948435 A      7/2014
CN        111227939 A      6/2020
WO     2020/263870 A1     12/2020

OTHER PUBLICATIONS

DaVinci Si HD Surgical System, User Manual. P/N 550650-5 Rev. C 2012.06. Intuitive Surgical. 40 pages, (2012).
(Continued)

*Primary Examiner* — T. Scott Fix
(74) *Attorney, Agent, or Firm* — McCarter & English, LLP

(57)     ABSTRACT

A drive assembly of a surgical robotic system is disclosed herein. In some embodiments, the drive assembly includes a first drive unit having a first drive unit face, a second drive unit having a second drive unit face, and a third drive unit having a third drive unit face. Each drive unit may include a plurality of motors configured to rotate a corresponding one of a plurality of drive elements about rotational axes perpendicular to the respective the respective drive unit face. the first drive unit, the second drive unit, and the third drive unit configured to be positioned about the drive assembly common axis with respect to a vertical plane passing through the drive assembly common axis such that an orientation and position of the first drive unit face mirrors those of second drive unit face, and the third drive unit face is bisected by the vertical plane.

17 Claims, 18 Drawing Sheets

(51) Int. Cl.
    *B25J 9/12*           (2006.01)
    *H02K 7/14*         (2006.01)

(58) Field of Classification Search
    USPC ....................................................... 74/490.05
    See application file for complete search history.

(56)              References Cited

U.S. PATENT DOCUMENTS

| | | |
|---|---|---|
| 2018/0221102 A1 | 8/2018 | Wang et al. |
| 2019/0076199 A1 | 3/2019 | Kline et al. |
| 2020/0405279 A1 | 12/2020 | Xu et al. |
| 2021/0113283 A1 | 4/2021 | Betsugi et al. |

OTHER PUBLICATIONS

DaVinci/SP, System User Manual. PN 553400-04 Rev. B 2022.06. Intuitive Surgical, Inc. 67 pages, (2022).
DaVinci/XI, System User Manual. PN 551400-15 Rev. B 2021.12, Intuitive Surgical Inc. 89 pages, (2021).
International Search Report and Written Opinion for Application No. PCT/US2023/013995, dated May 31, 2023, 42 pages.
International Preliminary Report on Patentability for Application No. PCT/US2023/013995, dated Sep. 6, 2024, 9 pages.

DRIVE ASSEMBLY FOR SURGICAL ROBOTIC SYSTEM

RELATED APPLICATION

This application claims priority to U.S. Provisional Application No. 63/314,090, filed Feb. 25, 2022, the entire contents of which are incorporated herein by reference.

BACKGROUND

Since its inception in the early 1990s, the field of minimally invasive surgery has rapidly grown. While minimally invasive surgery vastly improves patient outcome, this improvement comes at a cost to the surgeon's ability to operate with precision and ease. During conventional laparoscopic procedures, the surgeon typically inserts a laparoscopic instrument through multiple small incisions in the patient's abdominal wall. The nature of tool insertion through the abdominal wall constrains the motion of the laparoscopic instruments as the instruments are unable to move side-to-side without injury to the abdominal wall. Standard laparoscopic instruments are also limited in motion, and are typically limited to four axes of motion. These four axes of motion are movement of the instrument in and out of the trocar (axis 1), rotation of the instrument within the trocar (axis 2), and angular movement of the trocar in two planes while maintaining the pivot point of the trocar's entry into the abdominal cavity (axes 3 and 4). For over two decades, the majority of minimally invasive surgery has been performed with only these four degrees of motion. Moreover, prior systems require multiple incisions if the surgery requires addressing multiple different locations within the abdominal cavity.

Existing robotic surgical devices attempted to solve many of these problems. Some existing robotic surgical devices replicate non-robotic laparoscopic surgery with additional degrees of freedom at the end of the instrument. However, even with many costly changes to the surgical procedure, existing robotic surgical devices have failed to provide improved patient outcome in the majority of procedures for which they are used. Additionally, existing robotic devices create increased separation between the surgeon and surgical end-effectors. This increased separation causes injuries resulting from the surgeon's misunderstanding of the motion and the force applied by the robotic device. Because the degrees of freedom of many existing robotic devices are unfamiliar to a human operator, surgeons need extensive training on robotic simulators before operating on a patient in order to minimize the likelihood of causing inadvertent injury.

The surgical robotic device can include a remote surgeon console that communicates with a robot support system in the form of a patient cart. The patient cart can in turn communicate with a robotic unit that has a pair of robot arms and a corresponding camera assembly. The robotic unit can be coupled to the patient cart or station, which in turn serves to move the robot arms and camera assembly based on instructions from the remote console. Specifically, to control the robotic unit, the surgeon typically sits at the remote console and controls manipulators with his or her hands and/or feet. The surgeon's movements of the manipulators are than translated by suitable hardware and software into movement of selected components of the patient cart, which in turn via suitable motors and other mechanical connections selectively move the robot arms and the camera assembly.

A drawback of conventional surgical robotic devices is that the mechanical connection between the patient cart and the robotic unit can be large and cumbersome, and the translation of mechanical movement between the components can be inefficient.

A further drawback of conventional systems is that they do not employ an adequate number of drive elements, thus limiting the degree of movement of the robot arms and camera assembly.

A still further drawback of conventional systems is that the sterile barrier employed to isolate the patient cart from the surgical environment oftentimes does not provide adequate mechanical connections to allow sufficient mechanical connections between the cart and the disposable medical devices.

SUMMARY

Some embodiments of the present disclosure are directed to a drive assembly for a surgical robotic system. The drive assembly may include a first drive unit, a second drive unit, and a third drive unit. The first drive unit may have a first drive unit face, a plurality of first drive elements, and a plurality of first motors. Each of the plurality of first motors may be configured to rotate a corresponding one of the plurality of first drive elements about an axis perpendicular to the first drive unit face. The second drive unit may have a second drive unit face, a plurality of second drive elements, and a plurality of second motors. Each of the plurality of second motors may be configured to rotate a corresponding one of the plurality of second drive elements about an axis perpendicular to the second drive unit face. The third drive unit may have a third drive unit face, a plurality of third drive elements, and a plurality of third motors. Each of the plurality of third motors may be configured to rotate a corresponding one of the plurality of third drive elements about a rotation axis perpendicular to the third drive unit face. The drive assembly may include a drive assembly common axis corresponding to a cavity insertion axis. The first drive unit, the second drive unit, and the third drive unit may be configured to be positioned about the drive assembly common axis with respect to a vertical plane passing through the drive assembly common axis such that an orientation and position of the first drive unit face mirrors an orientation and position of the second drive unit face with respect to the vertical plane, and the third drive unit face is bisected by the vertical plane.

The drive assembly may have a first vector normal to the first drive unit face, a second normal to the second drive unit face, and a third vector normal to the third drive unit face are all perpendicular to the drive assembly common axis. The first vector, the second vector and the third vector may all lie in a common plane. The first drive unit may be configured to be positioned about the drive assembly common axis with the first vector at a first angle relative to the vertical plane as measured in the common plane. The second drive unit may be configured to be positioned about the drive assembly common axis with the second vector at a second angle relative to the vertical plane as measured in the common plane. The second angle may have a same magnitude and an opposite direction as the first angle.

The first drive unit, the second drive unit, and the third drive unit may be configured to be positioned with the first drive unit face opposite and substantially parallel to the second drive unit face, and with the third drive unit face substantially perpendicular to the first drive unit face.

The first drive unit may be configured to drive a first robotic arm assembly. The second drive unit may be configured to drive a second robotic arm assembly. The third drive unit may be configured to drive a camera assembly. Each of the plurality of first motors may have a drive shaft perpendicular to the first drive face. Each of the plurality of second motors may have a drive shaft perpendicular to the second drive face. Each of the plurality of third motors may have a drive shaft perpendicular to the third drive face.

The plurality of first drive elements may include a plurality of first drive-side crown elements, the plurality of second drive elements may include a plurality of second drive-side crown elements, and the plurality of third drive elements may include a plurality of third drive-side crown elements.

A mating surface of each of the first drive-side crown elements, a mating surface of each of the second drive-side crown elements, and a mating surface of each the third drive-side crown elements may be configured to engage a mating surface of a corresponding element of a drape plate to transmit rotational motion of the drive-side crown element to the corresponding element of the draft plate.

The first drive unit may further include a plurality of first motor couplings, each first motor coupling connecting one of the plurality of first drive-side crown elements to a corresponding one of the plurality of first motors to rotate the one of the plurality of first drive-side crown elements, each of the plurality of first motor couplings enabling the corresponding one of the plurality of drive-side crown elements to displace with respect to the corresponding one of the plurality of first motors to provide compliance for mating with the drive-side crown element.

The first drive unit face, the second drive unit face, and the third unit face may define a central channel through which the drive assembly common axis extends. The first drive unit may be configured to connect with a first cassette in the central channel. The second drive unit may be configured to connect with a second cassette in the central channel. The third drive unit is configured to connect with a third cassette in the central channel. The first drive unit may be configured to connect with the first cassette via a first drape plate. The second drive unit may be configured to connect with the second cassette via a second drape plate. The third drive unit may be configured to connect with the third cassette via a third drape plate.

The first drive unit may be configured to connect with the first cassette at the first drive unit face. The second drive unit may be configured to connect with the second cassette at the second drive unit face. The third drive unit may be configured to connect with the third cassette at the third drive unit face. The first drive unit may be configured to connect with the first cassette via a first drape plate disposed between the first drive unit face and the first cassette. The second drive unit may be configured to connect with the second cassette via a second drape plate disposed between the second drive unit face and the second cassette. The third drive unit may be configured to connect with the third cassette via a third drape plate disposed between third drive unit face and the third cassette.

The drive assembly may have a front end configured to be closer to the patient in use and a back end configured to be further from the patient in use. The first drive unit may be configured to connect with an interface portion of the first cassette inserted into the central channel from the back end of the drive assembly. The second drive unit may be configured to connect with an interface portion of the second cassette inserted into the central channel from the back end of the drive assembly. The third drive unit may be configured to connect with an interface portion of the third cassette inserted into the central channel from the back end of the drive assembly.

The first drive unit may be configured to slidably receive the interface portion of the first cassette inserted into the central channel from the back end of the drive assembly in a first direction parallel to the drive assembly common axis. The second drive unit may be configured to slidably receive the interface portion of the second cassette inserted into the central channel from the back end of the drive assembly in a second direction parallel to the drive assembly common axis. The third drive unit may be configured to slidably receive an interface portion of the third cassette inserted into the central channel from the back end of the drive assembly in a third direction parallel to the drive assembly common axis.

Some embodiments of the present disclosure is directed to a robotic subsystem for a surgical robotic system. The robotic subsystem may include a drive assembly in which the plurality of first drive elements may include a plurality of first drive-side crown elements, the plurality of second drive elements may include a plurality of second drive-side crown elements, and the plurality of third drive elements may include a plurality of third drive-side crown elements. The robotic subsystem may include a first cassette including a plurality of first spooley assemblies. Each of the plurality of first spooley assemblies may include a spool and a pulley and be configured to be driven by a corresponding one of the plurality of first drive-side crown elements. The robotic subsystem may include a second cassette including a plurality of second spooley assemblies. Each of the plurality of second spooley assemblies may include a spool and a pulley and be configured to be driven by a corresponding one of the plurality of second drive-side crown elements. The robotic subsystem may include a third cassette including a plurality of third spooley assemblies. Each of the plurality of third spooley assemblies may include a spool and a pulley and be configured to be driven by a corresponding one of the plurality of third drive-side crown elements.

The robotic subsystem may further include a first drape plate configured to be disposed between the first drive unit and the first cassette. The robotic subsystem may further include a second drape plate configured to be disposed between the second drive unit and the second cassette. The robotic subsystem may further include a third drape plate configured to be disposed between the third drive unit and the third cassette. The first cassette may be a first robotic arm assembly. The second cassette may be a second robotic arm assembly. The third cassette may be a camera assembly. The first arm assembly, the second arm assembly, and the camera assembly may be configured for insertion via a single trocar.

Embodiments of the present disclosure may provide a number of advantages. For example, use of the inverted "T" configuration described herein may allow for a plurality of motor units to be used while minimizing the opportunity for any portion of the drive assembly to contact a patient or operating table, or interfere with other instruments used during a procedure. Embodiments aligning the first arm assembly, the second arm assembly, and the camera assembly along a central channel through which the drive assembly common axis extends may allow for insertion of each of the first arm assembly, the second arm assembly, and the camera assembly via a single trocar. Use of the single trocar may reduce the complexity and/or duration of the surgical procedure and may enhance the procedure and recover for the patient. Embodiments in which the cassette is slidably removable from the drive unit, and in particular where the cassette may be removed from the rear of the drive unit (e.g., away from the patient) may support safe and rapid removal of robotic arms from the patient in an emergency situation, or after completion of the surgery. Embodiments in which a drape plate is disposed between the drive units and the cassettes may establish a sanitary barrier to maintain the drive units in a sanitary state and facilitate the re-use of the drive units.

BRIEF DESCRIPTION OF THE DRAWINGS

These and other features and advantages of embodiments of the present disclosure will be more fully understood by reference to the following detailed description in conjunction with the drawings in which like reference numerals refer to like elements throughout the different views. The drawings illustrate principals of the presents disclosure and are not necessarily to scale, although some show relative dimensions.

DETAILED DESCRIPTION

Figure 1:
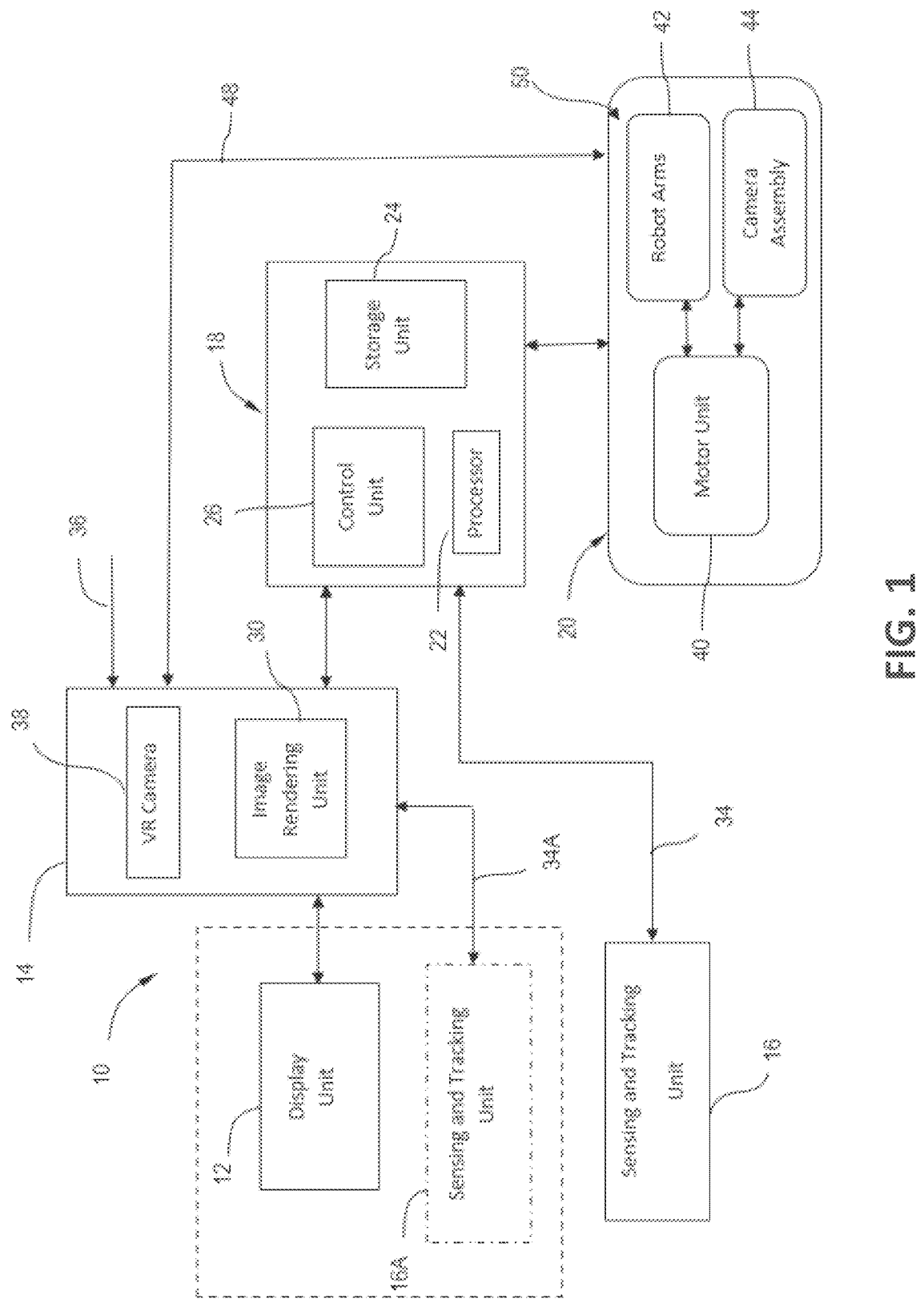
FIG. 1 schematically depicts a surgical robotic system in accordance with some embodiments.

Some embodiments described herein are directed to a robot support system "RSS" (also referred to as a "patient cart") for a surgical robotic system having a series of drives or motors for moving components, such as robot arms and a camera assembly, of a surgical robotic unit. The robot support system can include a selected arrangement of drives or drive units for interacting and interfacing with the robot arm subassemblies and a camera subassembly.

In the following description, numerous specific details are set forth regarding systems, devices, assemblies, and methods of embodiments and environments in which the embodiments may operate, in order to provide a thorough understanding of the disclosed subject matter. It will be apparent to one skilled in the art, however, that the disclosed subject matter may be practiced without such specific details, and that certain features, which are well known in the art, are not described in detail in order to avoid complication and enhance clarity of the disclosed subject matter. In addition, it will be understood that any examples provided below are merely illustrative and are not to be construed in a limiting manner, and that it is contemplated by the present inventors that other systems, apparatuses, and/or methods can be employed to implement or complement the teachings of the present invention and are deemed to be within the scope of the present invention.

Although some embodiments are described as using a plurality of units to perform the exemplary process, it is understood that the exemplary processes may also be performed by one or a plurality of modules. Additionally, it is understood that the term controller, control unit, computing unit, and the like refers to a hardware device that includes a memory and a processor and is specifically programmed to execute the processes described herein. The memory is configured to store the modules and the processor is specifically configured to execute the functions and operations associated with the modules to perform the one or more processes that are described herein.

Furthermore, control logic of the some methods or processes may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN). The control logic can also be implemented using application software that is stored in suitable storage and memory and processed using known processing devices. The control unit as described herein can be implemented using any selected computer hardware that employs a processor, storage and memory.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Some embodiments of systems disclosed include a patient cart that is designed for use with one or more surgical robotic systems. Embodiments disclosed herein may be employed in connection with any type of surgical system, including for example robotic surgical systems, straight-stick type surgical systems, and laparoscopic systems. Additionally, some embodiments disclosed herein may be used in other non-surgical systems in which a user requires access to a myriad of information while controlling a device or apparatus. In some embodiments, systems, assemblies and methods descried herein systems may be employed as part of a virtual reality surgical system.

The surgical robotic system 10 employs a robotic subsystem 20 that includes a robotic unit 50 that can be inserted into a patient via a trocar through a single incision point or site. The robotic unit 50 is small enough to be deployed in vivo at the surgical site and is sufficiently maneuverable when inserted to be able to move within the body to perform various surgical procedures at multiple different points or sites. The robotic unit 50 includes multiple separate robotic arms that are deployable within the patient along different or separate axes. Further, a surgical camera assembly can also be deployed along a separate axis and form part of the robotic unit 50. Thus, the robotic unit 50 employs multiple different components, such as a pair of robotic arms and a surgical or robotic camera assembly, each of which are deployable along different axes and are separately manipulatable, maneuverable, and movable. The robotic arms and the camera assembly that are disposable along separate and manipulatable axes is referred to herein as the Split Arm (SA) architecture. The SA architecture is designed to simplify and increase efficiency of the insertion of robotic surgical instruments through a single trocar at a single insertion site, while concomitantly assisting with deployment of the surgical instruments into a surgical ready state as well as the subsequent removal of the surgical instruments through the trocar. By way of example, a surgical instrument can be inserted through the trocar to access and perform an operation in vivo in the abdominal cavity of a patient. In some embodiments, various surgical instruments may be utilized, including but not limited to robotic surgical instruments, as well as other surgical instruments known in the art.

The system and method disclosed herein can be incorporated and utilized with the robotic surgical device and associated system disclosed for example in U.S. Pat. No. 10,285,765 and in PCT patent application Serial No. PCT/US20/39203, and/or with the camera assembly and system disclosed in United States Publication No. 2019/0076199, where the content and teachings of all of the foregoing patents, patent applications and publications are incorporated herein by reference. The robotic unit 50 can form part of the robotic subsystem 20, which in turn forms part of a surgical robotic system 10 that includes a surgeon or user workstation that includes appropriate sensors and displays, and a robot support system (RSS), for interacting with and supporting the robotic unit. The robotic subsystem 20 can include, in one embodiment, a portion of the RSS, such as for example a motor assembly and associated mechanical linkages, and the surgical robotic unit 50 can include one or more robot arms and one or more camera assemblies. The surgical robotic unit 50 can provide multiple degrees of freedom such that the robotic unit can be maneuvered within the patient into a single position or multiple different positions. In one embodiment, the robot support system can be directly mounted to a surgical table or to the floor or ceiling within an operating room. In another embodiment, the mounting is achieved by various fastening means, including but not limited to, clamps, screws, or a combination thereof. In still other embodiments, the structure may be free standing and portable or movable. The robot support system can mount the motor assembly that is coupled to the surgical robotic unit and can include gears, motors, drivetrains, electronics, and the like, for powering the components of the surgical robotic unit.

The robot arms and the camera assembly are capable of multiple degrees of freedom of movement. According to one practice, when the robot arms and the camera assembly are inserted into a patient through the trocar, they are capable of movement in at least the axial, yaw, pitch, and roll directions. The robot arm assemblies are designed to incorporate and utilize a multi-degree of freedom of movement robotic arm with an end effector region mounted at a distal end thereof that corresponds to a wrist and hand area or joint of the user. In other embodiments, the working end (e.g., the end effector end) of the robot arm is designed to incorporate and utilize other robotic surgical instruments, such as for example the surgical instruments set forth in U.S. Publ. No.
2018/0221102, the contents of which are herein incorporated
by reference.

FIG. 1 is a schematic block diagram illustration of a
surgical robotic system 10 according to some embodiments.
The system 10 includes a display device or unit 12, a virtual
reality (VR) computing unit 14, a sensing and tracking unit
16, a computing unit 18, and a robotic subsystem 20. The
display unit 12 can be any selected type of display for
displaying information, images or video generated by the
VR computing unit 14, the computing unit 18, and/or the
robotic subsystem 20. The display unit 12 can include or
form part of, for example, a head-mounted display (HMD),
a screen or display, a three-dimensional (3D) screen, and the
like. The display can form part of the surgeon or user's work
station. While the embodiment depicted in FIG. 1 depicts the
surgical robotic system 10 as including the VR computing
unit 14, in other embodiments VR computing unit 14 may be
omitted.

In embodiments, the display device or unit 12 may be any
selected type of display for displaying information, images
or video generated by an image computer, the computing
unit 18, and/or the robotic subsystem 20. A visualization
system used in embodiments can include or form part of, for
example, a head-mounted display (HMD), an augmented
reality (AR) display (e.g., an AR display, or AR glasses in
combination with a screen or display), a screen or a display,
a two-dimensional (2D) screen or display, a three-dimen-
sional (3D) screen or display, and the like.

The display unit 12 can also include an optional sensor
and tracking unit 16A, such as can be found in commercially
available head mounted displays. The sensing and tracking
units 16 and 16A can include one or more sensors or
detectors that are coupled to a user of the system, such as for
example a nurse or a surgeon. The sensors can be coupled to
the arms of the user and if a head-mounted display is not
used, then additional sensors can also be coupled to a head
and/or neck region of the user. The sensors in this arrange-
ment are represented by the sensor and tracking unit 16. If
the user employs a head-mounted display, then the eyes,
head and/or neck sensors and associated tracking technology
can be built-in or employed within that device, and hence
form part of the optional sensor and tracking unit 16A. The
sensors of the sensor and tracking unit 16 that are coupled
to the arms of the surgeon can be preferably coupled to
selected regions of the arm, such as for example the shoulder
region, the elbow region, the wrist or hand region, and if
desired the fingers. According to one practice, the sensors
from part of a pair of hand controllers that are manipulated
by the surgeon. The sensors generate position data indicative
of the position of the selected portion of the user. The
sensing and tracking units 16 and/or 16A can be utilized to
control movement of the camera assembly 44 and the
robotic arms 42 of the robotic subsystem 20. The robotics
arms 42 and the camera assembly 44 may be referred to as
a "cassette." As such, the sensing and tracking units 16
and/or 16A can be utilized to control movement of a
cassette. The position data 34 generated by the sensors of the
sensor and tracking unit 16 can be conveyed to the com-
puting unit 18 for processing by a processor 22. The
computing unit 20 can determine or calculate from the
position data 34 the position and/or orientation of each
portion of the surgeon's arm and convey this data to the
robotic subsystem 20. According to an alternate embodi-
ment, the sensing and tracking unit 16 can employ sensors
coupled to the torso of the surgeon or any other body part.
Further, the sensing and tracking unit 16 can employ in addition to the sensors an Inertial Momentum Unit (IMU)
having for example an accelerometer, gyroscope, magne-
tometer, and a motion processor. The addition of a magne-
tometer is standard practice in the field as magnetic heading
allows for reduction in sensor drift about the vertical axis.
Alternate embodiments also include sensors placed in sur-
gical material such as gloves, surgical scrubs, or a surgical
gown. The sensors may be reusable or disposable. Further,
sensors can be disposed external of the user, such as at fixed
locations in a room, such as an operating room. The external
sensors can generate external data 36 that can be processed
by the computing unit and hence employed by the system
10. In other embodiments, there are sensors located on a
mechanical linkage that the user manipulates. The sensors
generate signals that serve as inputs to be processed by the
computing unit. According to another embodiment, when
the display unit 12 is a head mounted device that employs an
associated sensor and tracking unit 16A, the device gener-
ates tracking and position data 34A that is received and
processed by the VR computing unit 14. Further, the sensor
and tracking unit 16 include if desired a hand controller. The
displays, sensing and tracking units, VR computing unit and
the like can form part of a surgeon or remote work station.

In the embodiment where the display is a HMD, the
display unit 12 can be a virtual reality head-mounted display,
such as for example the Oculus Rift, the Varjo VR-1 or the
HTC Vive Pro Eye. The HMD can provide the user with a
display that is coupled or mounted to the head of the user,
lenses to allow a focused view of the display, and a sensor
and/or tracking system 16A to provide position and orien-
tation tracking of the display. The position and orientation
sensor system can include for example accelerometers,
gyroscopes, magnetometers, motion processors, infrared
tracking, eye tracking, computer vision, emission and sens-
ing of alternating magnetic fields, and any other method of
tracking at least one of position and orientation, or any
combination thereof. As is known, the HMD can provide
image data from the camera assembly 44 to the right and left
eyes of the surgeon. In order to maintain a virtual reality
experience for the surgeon, the sensor system can track the
position and orientation of the surgeon's head, and then
relay the data to the VR computing unit 14, and if desired to
the computing unit 18. The computing unit 18 can further
adjust the pan and tilt of the camera assembly 44 of the robot
to follow the movement of the user's head.

The sensor or position data 34A generated by the sensors
if associated with the HMD, such as for example associated
with the display unit 12 and/or tracking unit 16A, can be
conveyed to the computing unit 18 either directly or via the
VR computing unit 14. Likewise, the tracking and position
data 34 generated by the other sensors in the system, such as
from the sensing and tracking unit 16 that can be associated
with the user's arms and hands, can be conveyed to the
computing unit 18. The tracking and position data 34, 34A
can be processed by the processor 22 and can be stored for
example in the storage unit 24. The tracking and position
data 34, 34A can also be used by the control unit 26, which
in response can generate control signals for controlling
movement of one or more portions of the robotic subsystem
20. The surgical robotic system 10 can include a surgeon or
user workstation, the robot support system (RSS), and the
robotic subsystem 20, and the robotic subsystem 20 can
include the motor unit 40 and an implantable robotic unit 50
that includes one or more robot arms 42 and one or more
camera assemblies 44. According to another embodiment,
the motor unit 40 can form part of the robot support system.
The implantable robot arms 42 and the camera assembly 44 can form part of a single support axis robotic unit or subsystem, such as that disclosed and described in U.S. Pat. No. 10,285,765, or can form part of a split arm (SA) architecture robot system, such as that disclosed and described in PCT patent application no. PCT/US20/39203.

The control signals generated by the control unit 26 can be received by the motor unit 40 of the robotic subsystem 20. The motor unit 40 can include a series of servomotors and gears that are configured for driving separately the robot arms 42 and the cameras assembly 44 of the robotic subsystem 50. The robot arms 42 can be controlled to follow the scaled-down movement or motion of the surgeon's arms as sensed by the associated sensors. The robot arms 42 can have portions or regions that can be associated with movements associated with the shoulder, elbow, and wrist joints as well as the fingers of the user. For example, the robotic elbow joint can follow the position and orientation of the human elbow, and the robotic wrist joint can follow the position and orientation of the human wrist. The robot arms 42 can also have associated therewith end regions that can terminate in end-effectors or graspers that follow the movement of one or more fingers of the user, such as for example the index finger as the user pinches together the index finger and thumb. While the arms of the robot follow movement of the arms of the user, the robot shoulders are fixed in position. In one embodiment, the position and orientation of the torso of the user is subtracted from the position and orientation of the users arms. This subtraction allows the user to move his or her torso without the robot arms moving.

The robot camera assembly 44 is configured to provide the surgeon with image data 48, such as for example a live video feed of an operation or surgical site, as well as enable a surgeon to actuate and control the cameras forming part of the camera assembly 44. The camera assembly 44 preferably includes a pair of cameras, the optical axes of which are axially spaced apart by a selected distance, known as the inter-camera distance, to provide a stereoscopic view or image of the surgical site. The surgeon can control the movement of the cameras either through movement of a head-mounted display or via sensors coupled to the head of the surgeon, or by using a hand controller or sensors tracking the user's head or arm motions, thus enabling the surgeon to obtain a desired view of an operation site in an intuitive and natural manner. The cameras are movable in multiple directions, including for example in the yaw, pitch and roll directions, as is known. The components of the stereoscopic cameras can be configured to provide a user experience that feels natural and comfortable. In some embodiments, the interaxial distance between the cameras can be modified to adjust the depth of the operation site perceived by the user.

According to one embodiment, the camera assembly 44 can be actuated by movement of the surgeon's head. For example, during an operation, if the surgeon wishes to view an object located above the current field of view (FOV), the surgeon looks in the upward direction, which results in the stereoscopic cameras being rotated upward about a pitch axis from the user's perspective. The image or video data 48 generated by the camera assembly 44 can be displayed on the display unit 12. If the display unit 12 is a head-mounted display, the display can include the built-in tracking and sensor system 16A that obtains raw orientation data for the yaw, pitch and roll directions of the HMD as well as positional data in Cartesian space (x, y, z) of the HMD. However, alternative tracking systems may be used to provide supplementary position and orientation tracking data of the display in lieu of or in addition to the built-in tracking system of the HMD.

The image data 48 generated by the camera assembly 44 can be conveyed to the virtual reality (VR) computing unit 14 and can be processed by the VR or image rendering unit 30. The image data 48 can include still photographs or image data as well as video data. The VR rendering unit 30 can include suitable hardware and software for processing the image data and then rendering the image data for display by the display unit 12, as is known in the art. Further, the VR rendering unit 30 can combine the image data received from the camera assembly 44 with information associated with the position and orientation of the cameras in the camera assembly, as well as information associated with the position and orientation of the head of the surgeon. With this information, the VR rendering unit 30 can generate an output video or image rendering signal and transmit this signal to the display unit 12. That is, the VR rendering unit 30 renders the position and orientation readings of the hand controllers and the head position of the surgeon for display in the display unit, such as for example in a HMD worn by the surgeon.

The VR computing unit 14 can also include a virtual reality (VR) camera unit 38 for generating one or more virtual reality (VR) cameras for use or emplacement in the VR world that is displayed in the display unit 12. The VR camera unit 38 can generate one or more virtual cameras in a virtual world, and which can be employed by the system 10 to render the images for the head-mounted display. This ensures that the VR camera always renders the same views that the user wearing the head-mounted display sees to a cube map. In one embodiment, a single VR camera can be used and in another embodiment separate left and right eye VR cameras can be employed to render onto separate left and right eye cube maps in the display to provide a stereo view. The FOV setting of the VR camera can self-configure itself to the FOV published by the camera assembly 44. In addition to providing a contextual background for the live camera views or image data, the cube map can be used to generate dynamic reflections on virtual objects. This effect allows reflective surfaces on virtual objects to pick up reflections from the cube map, making these objects appear to the user as if they're actually reflecting the real world environment.

The robotic unit 50 can employ multiple different robotic arms 42 that are deployable along different or separate axes. Further, the camera assembly 44, which can employ multiple different camera elements, can also be deployed along a common separate axis. Thus, the robotic unit 50 employs multiple different components, such as a pair of separate robotic arms and a camera assembly 44, which are deployable along different axes. Further, the robot arms 42 and the camera assembly 44 are separately manipulatable, maneuverable, and movable. The robotic subsystem 20, which includes the robot arms and the camera assembly, is disposable along separate manipulatable axes to form the SA architecture. The SA architecture is designed to simplify and increase efficiency of the insertion of robotic surgical instruments through a single trocar at a single insertion point or site, while concomitantly assisting with deployment of the surgical instruments into a surgical ready state, as well as the subsequent removal of the surgical instruments through the trocar. By way of example, a surgical instrument can be inserted through the trocar to access and perform an operation in vivo in a body cavity of a patient. In some embodiments, various surgical instruments may be utilized, including but not limited to robotic surgical instruments, as well as other surgical instruments known in the art.

In some embodiments, the robotic subsystem 20 is supported by the RSS with multiple degrees of freedom such that the robotic arms 42 and camera assembly 44 can be maneuvered within the patient into a single position or multiple different positions. In one embodiment, the robotic subsystem 20 can be directly mounted to the RSS. In other embodiments, the RSS of the surgical robotic system 10 can optionally include the motor unit 40 that is coupled to the robotic unit 50 at one end and to an adjustable support member or element at an opposed end. Alternatively, as shown herein, the motor unit 40 can form part of the robotic subsystem 20. The motor unit 40 can include gears, one or more motors, drivetrains, electronics, and the like, for powering and driving one or more components of the robot arms and the camera assembly (e.g., robotic unit 50). The robotic unit 50 can be selectively coupled to the motor unit 40. According to one embodiment, the RSS can include a support member that has the motor unit 40 coupled to a distal end thereof. The motor unit 40 in turn can be coupled to the camera assembly 44 and to each of the robot arms 42. The support member can be configured and controlled to move linearly, or in any other selected direction or orientation, one or more components of the robotic unit 50.

The motor unit 40 can also provide mechanical power, electrical power, mechanical communication, and electrical communication to the robotic unit 50, and can further include an optional controller for processing input data from one or more of the system components (e.g., the display 12, the sensing and tracking unit 16, the robot arms 42, the camera assembly 44, and the like), and for generating control signals in response thereto. The motor unit 40 can also include a storage element for storing data. Alternatively, the motor unit 40 can be controlled by the computing unit 18. The motor unit 40 can thus generate signals for controlling one or more motors that in turn can control and drive the robot arms 42, including for example the position and orientation of each articulating joint of each arm, as well as the camera assembly 44. The motor unit 40 can further provide for a translational or linear degree of freedom that is first utilized to insert and remove each component of the robotic unit 50 through a suitable medical device, such as a trocar. The motor unit 40 can also be employed to adjust the inserted depth of each robot arm 42 when inserted into the patient through the trocar.

Figures 2A, 2B:
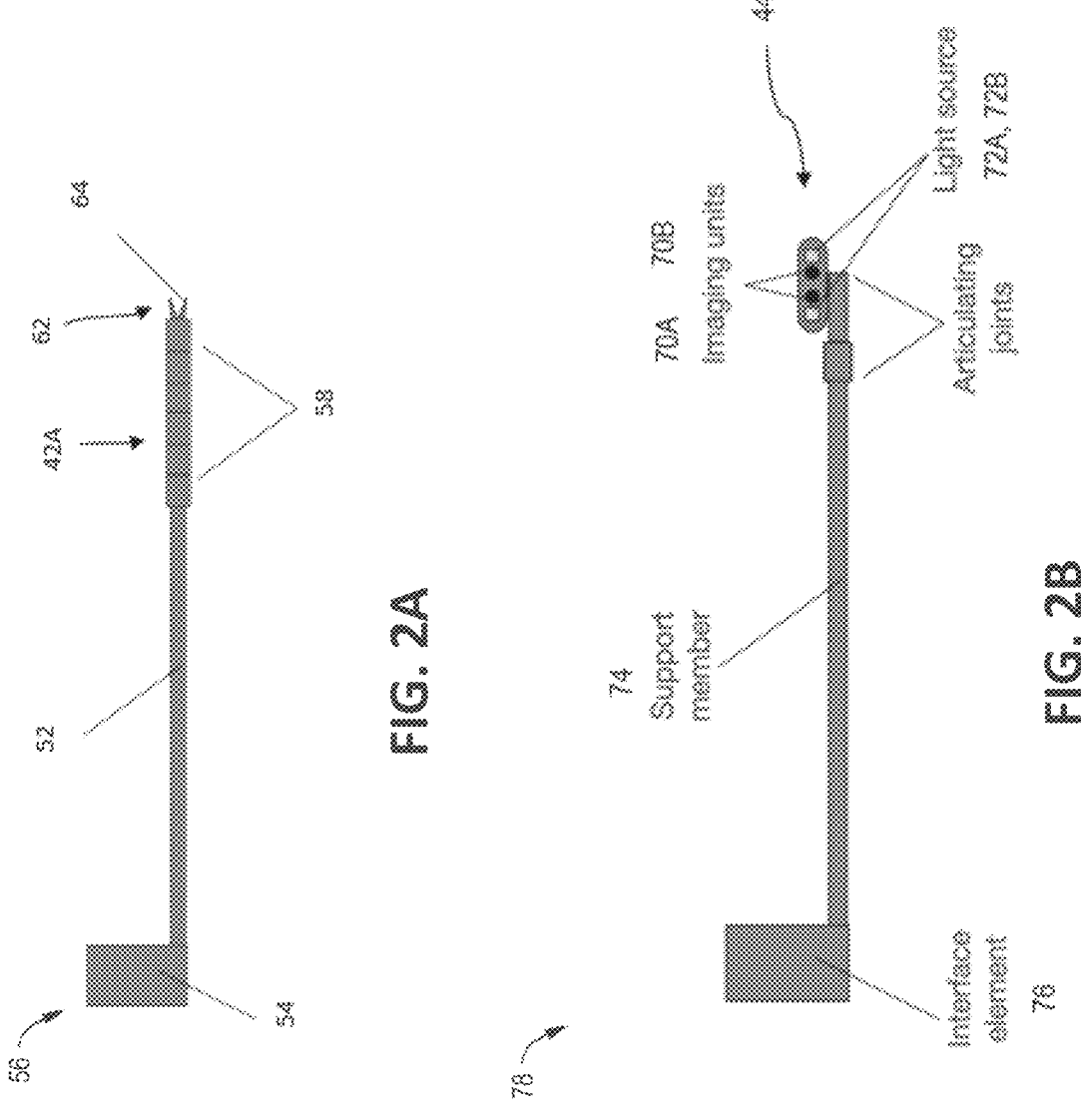
FIG. 2A schematically depicts a robot arm subassembly of the surgical robotic system in accordance with some embodiments.
FIG. 2B schematically depicts a camera subassembly of the surgical robotic system in accordance with some embodiments.

FIGS. 2A and 2B illustrate the general design of selected components of the robotic subsystem 20 in accordance with some embodiments. For example, FIG. 2A illustrates a robot arm subassembly 56 in accordance with some embodiments. The illustrated robot arm subassembly 56 includes an axially extending support member 52 that has an interface element 54 coupled to a proximal end and a robot arm 42A coupled to an opposed distal end. The support member 52 serves to support the robot arm 42A when mounted thereto, and can further function as a conduit for mechanical power, electrical power, and communication. For the sake of simplicity, only the first robot arm 42A is shown, although the second robot arm 42B or subsequent arms can be similar or identical. The interface element 54 is configured to connect to the motor unit 40 for transferring a driving force therefrom and any associated signals, via the support element 52, to the robot arm 42A. The interface element can have any selected shape and size is preferably configured to engage with a driving end of a drive unit of the motor unit 40. In one embodiment, the interface element 54, 76 can employ a series of electrical contacts and a series of mechanical linkage devices, such as pulleys, each having a rotational axis. In another embodiment, the mechanical pulleys can each include a male spline protruding from the surface of the interface element. Each male spline is configured to mate with a female spline located on the drive element and thus provide for the transmission of mechanical power in the form of torque. In still another embodiment, the pulleys can employ one or more female splines that engage with one or more male splines that are located on the drive elements. In still other embodiments, the mechanical power from the drive elements can be transferred to the interface elements by other mating type surfaces as is known in the art. Further, the illustrated robot arm 42A can include a series of articulation sections 58 that form joint sections that correspond to the joints of a human arm. As such, the articulation sections 58 can be constructed and combined to provide for rotational and/or hinged movement to emulate different portions of the human arm, such as for example the shoulder joint or region, elbow joint or region, and the wrist joint or region. The articulation sections 58 of the robot arm 42A are constructed to provide cable-driven, rotational movement, for example, but within the confines of reasonable rotational limits. The articulation sections 58 are configured to provide maximum torque and speed with minimum size. In an alternate embodiment, the articulation sections 58 can include spherical joints, thus providing for multiple, such as two or three, rotational degrees of freedom in a single joint.

In one embodiment, each articulation section 58 can be oriented orthogonally, relative to a starting point, to an adjacent articulation section. Further, each articulation section 58 can be cable driven and can have a Hall Effect sensor array associated therewith for joint position tracking. In another embodiment, the articulation section can include inertial measurement units or magnetic tracking solutions, such as those provided by Polhemus, USA, that are integrated therein to provide for joint position tracking or estimation. Further, communication wires for the sensors as well as the mechanical drive cables can be routed proximally through an inner chamber of the support member 52 to the proximal interface element 54. The robot arm 42A can also include an end portion 62 that can have coupled thereto one or more surgical tools, as is known in the art. According to one embodiment, an end effector or grasper 64 can be coupled to the end portion 62. The end effector can mimic movement of one or more of the surgeon's fingers.

FIG. 2B illustrates the camera subassembly 78 in accordance with some embodiments. The illustrated camera assembly can include an axially extending support member 74 that has an interface element 76 coupled to a proximal end and a camera assembly 44 coupled to an opposed distal end. The illustrated camera assembly 44 can include a pair of camera elements 70A, 70B. The camera assembly can be connected or coupled to the support member 74 in such a manner to allow movement of the camera assembly relative to the support member in the yaw and pitch directions. The camera elements can be separate and distinct relative to each other or can be mounted in a common housing, as shown. Each of the camera elements 70A, 70B can have a light source 72A, 72B, respectively, associated therewith. The light source can be disposed at any selected location relative to the camera elements. The support member 74 serves to support the camera assembly 44 when mounted thereto, and can further function as a conduit for mechanical power, electrical power, and communication. The interface element 76 is configured to connect to the motor unit 40 for transferring a driving force therefrom and any associated signals, via the support element 52, to the camera assembly 44.

Figure 3:
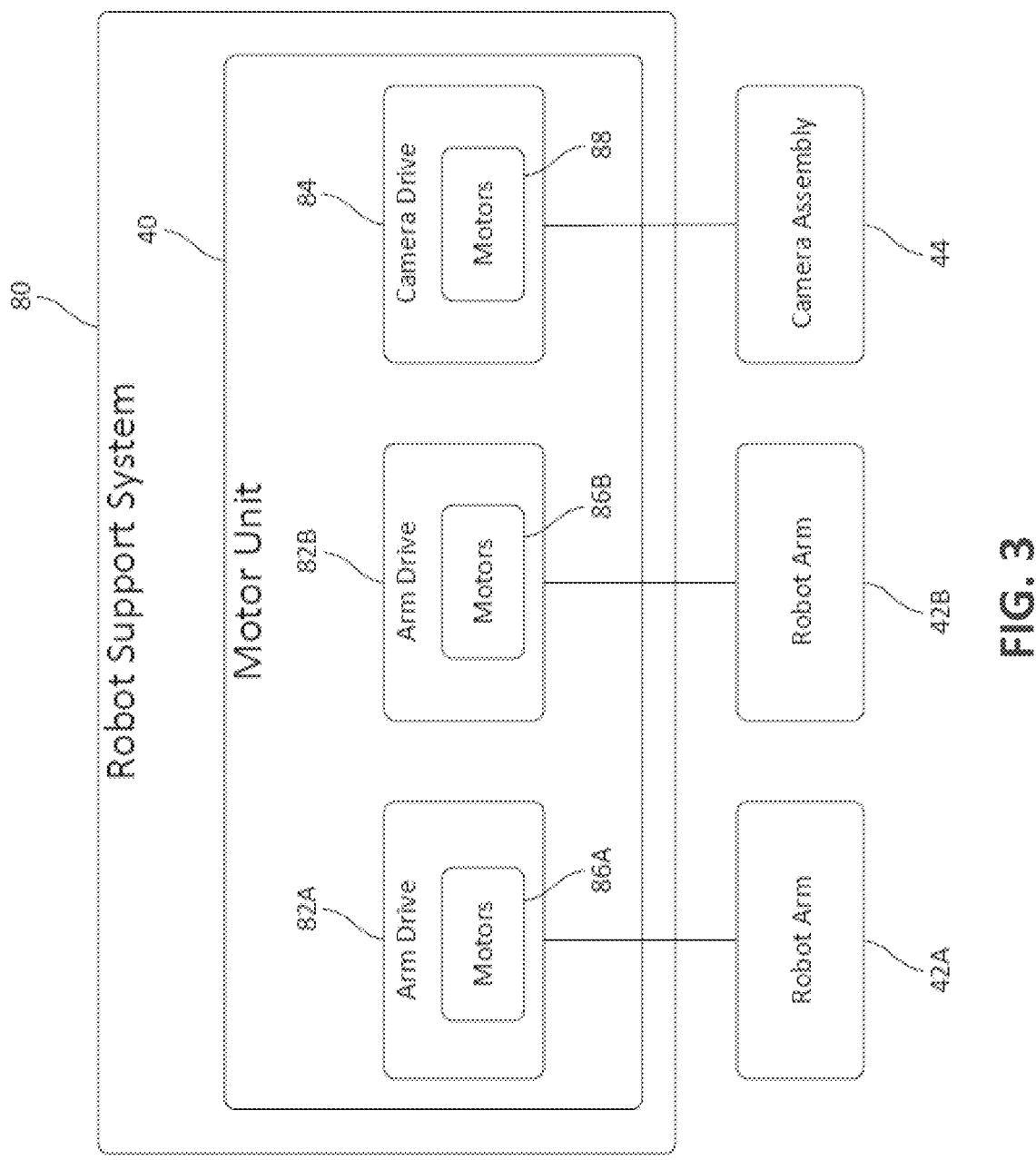
FIG. 3 schematically depicts a robot support system of the surgical robotic system in accordance with some embodiments.

FIG. 3 is a schematic representation of an RSS or patient cart 80 in accordance with some embodiments. In the illustrated embodiment, the RSS 80 includes the motor unit 40. The motor unit 40 can include multiple different arm drive units 82A and 82B or 81A, and 81B, and a camera drive unit 84 or 81C, all of which are configured and arranged into a single cohesive form factor. The arm drive units 82A and 82B or 81A and 81B engage with the interface element 54 of the robot arm subassembly 56. The camera drive unit 84 or 81C engages with the interface element 76 of the camera subassembly 78. The drive units 82A and 82B or 81A and 81B move or drive the robot arms 42A and 42B, respectively, and the camera drive unit 84 moves or drives the camera subassembly 78. The arm drive units 82A and 82B or 81A, and 81B include motors 86A and 86B, respectively, for controlling movement of the robot arms 42A and 42B. Specifically, the arm drive units 82A and 82B or 81A, and 81B can include a selected number of motors 86A and 86B, respectively. According to one embodiment, each of the arm drive units can include fourteen motors to provide multiple degrees of freedom (e.g., seven degrees of freedom) of movement of the robot arms. One of ordinary skill in the art will readily recognize that the arm drive units can include any selected number of motors provided that the number of motors included provides the desired degree of freedom of movements of the robot arms. Furthermore, the camera drive unit 84 can include any selected number of motors, such as for example six motors 88, for controlling movement of the camera assembly 44. The numerous degrees of freedom of the robot arms and the camera assembly determines the number of motors in each of the drive units. Stated another way, a first drive unit can include more motors relative to a different second drive unit when the cassette or interface housing associated with the first drive unit has a greater number of degrees of freedom relative to another cassette or interface housing associated with the second drive unit. The drive units each ride or move along a corresponding rail element, allowing the drive units to plunge toward the patient independently of one another. The drives elements align the robot arms and the camera assembly so that they can be inserted through the trocar.

Figure 4:
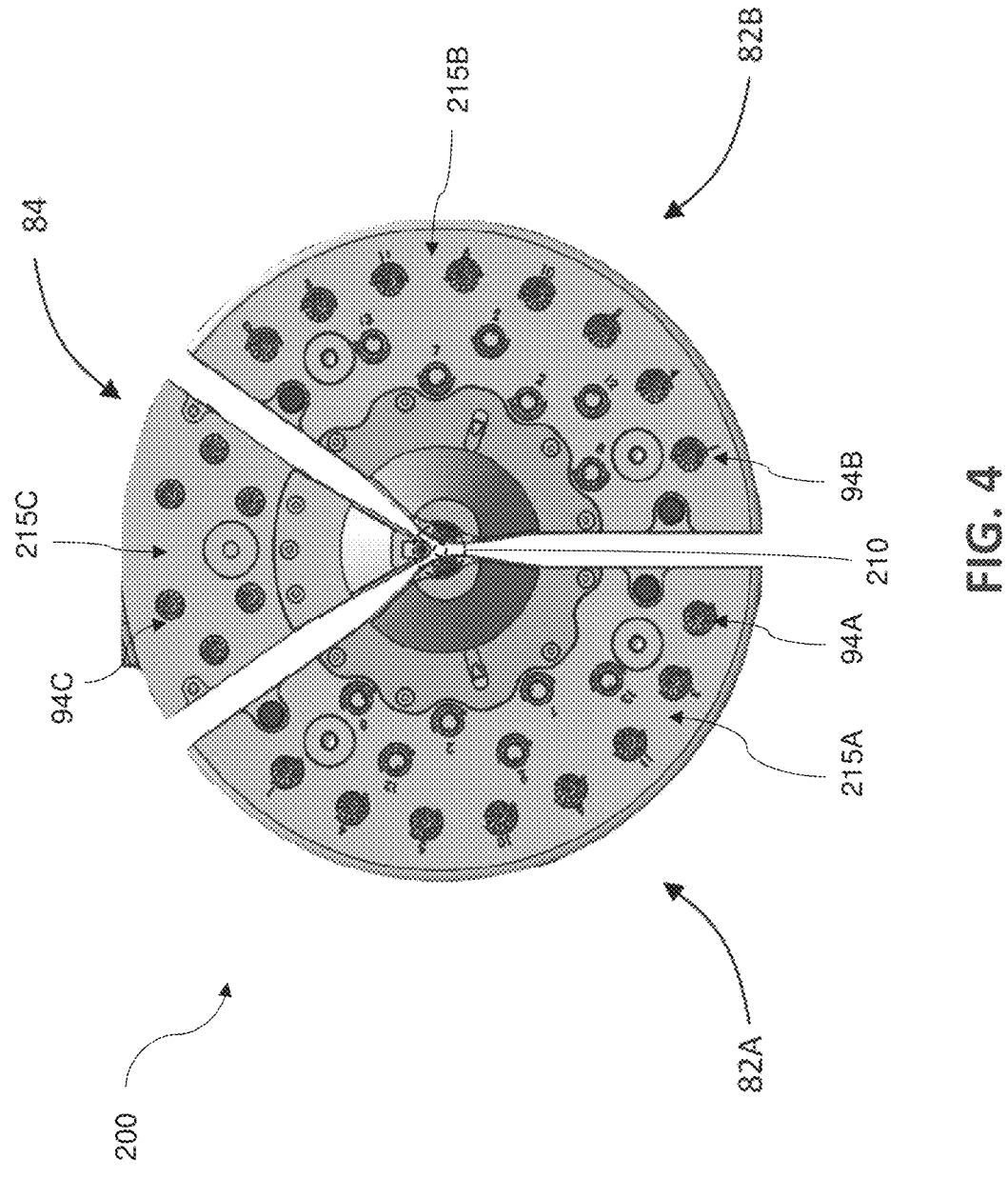
FIG. 4 depicts an end view of drive units or drive assemblies of the surgical robotic system having a circular or drum form factor in accordance with some embodiments.

FIG. 4 depicts a front (patient side) view of drive units 82A, 82B, 84, of a drive assembly 200 showing drive unit faces 215A, 215B, 215C in accordance with some embodiments. In this embodiment, the drive assembly 200 including the drive units 84, 82A, 82B collectively, has a drum form factor that has a generally circular cross-section. The depicted embodiment provides three drive units 82A, 82B, 84 collectively having a drum form factor, but the present disclosure is not limited to a particular number of drive units.

To install the robot arm subassemblies 56 of FIG. 2A into the arm drive units 82A and 82B, the interface housing elements 54 of the robot arm subassemblies 56 are pushed directly onto the front face (patient side) of the arm drive units 82A and 82B, respectively, in a direction normal to the face, thereby securing the robot arm subassemblies 56 to the arm drive units 82A and 82B. Similarly, to install the camera subassembly 78 of FIG. 2B, the interface housing element 76, the camera subassembly 78 is pushed directly onto the front face of the camera drive unit 84. In this embodiment, the drive shafts (not shown) of the motors of each drive unit 82A, 82B, 84 are perpendicular to the front face of the drive unit and face towards the patient.

Each of the drive units 82A, 82B, 84 has a drive unit face 215A, 215B, and 215C. Each of the drive units 82A, 82B, 84 includes a plurality of drive elements. The drive elements may include a plurality of drive-side crown elements 94A. The mating surface of each of the drive-side crown elements

94A may be configured to engage a corresponding mating surface of a corresponding crown element to transmit rotational motion of the drive-side crown element (94A, 94B, 94C).

FIGS. 5A-7 depict embodiments of dive assemblies in which the first drive unit, the second drive unit and the third drive unit are configured to be positioned about a drive assembly common axis with respect to a vertical plane passing through the drive assembly common axis such that an orientation and position of the first drive unit face mirrors an orientation and position of the second drive unit face, and the third drive unit face is bisected by the vertical plane in accordance with some embodiments when mounted on the patient cart. This may be referred to as an inverted "Y" or upside-down Y configuration and orientation. In embodiments in which the first drive unit face is parallel to the second drive unit face, this is a type of inverted Y or upside-down Y configuration that is referred to as an inverted "T" (or upside-down T) shaped configuration and orientations.

Figure 5A:
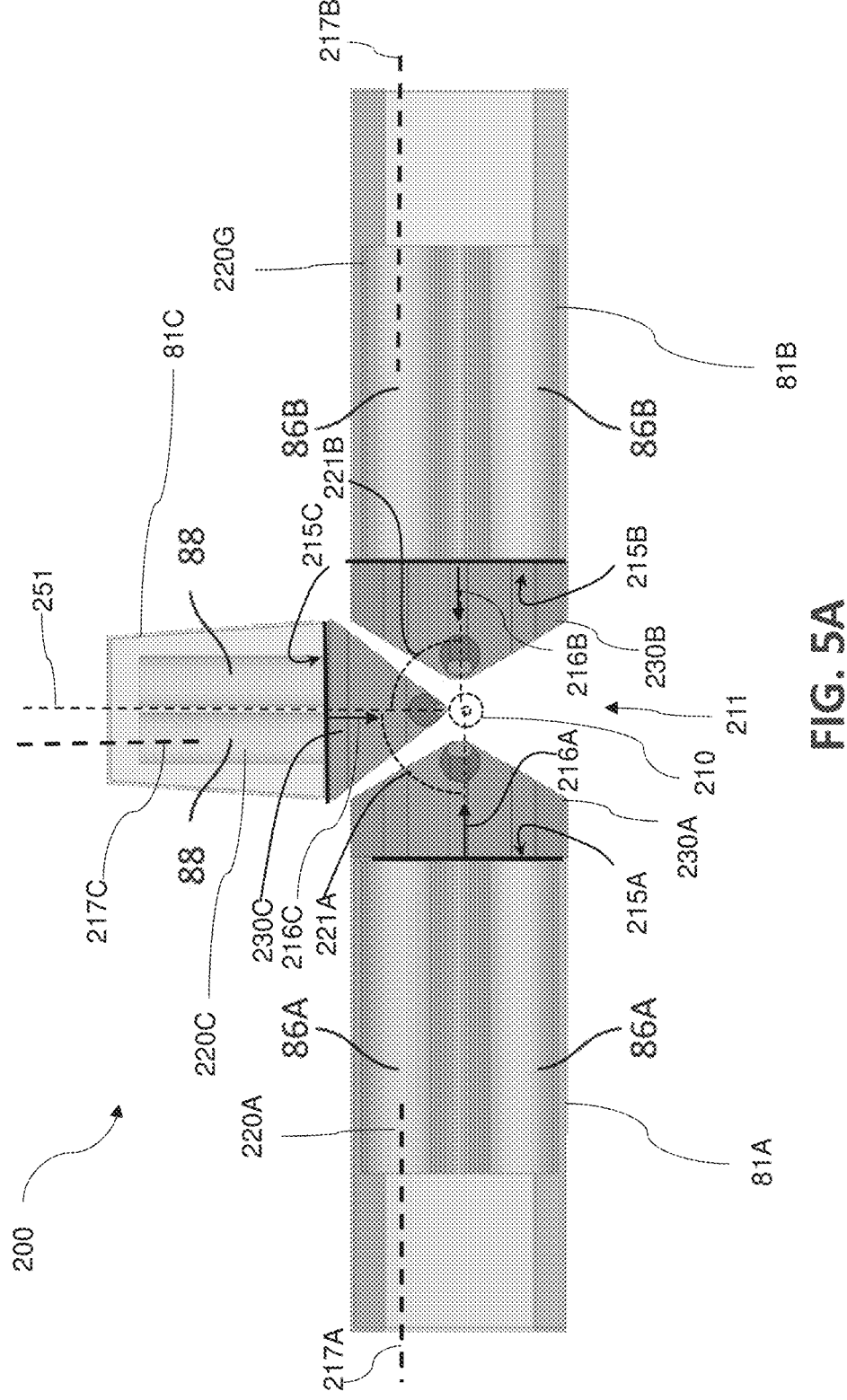
FIG. 5A depicts a drive assembly of a surgical robotic system having a lute form factor and in an inverted "T" configuration and mounted cassettes in accordance with some embodiments.
Figure 5B:
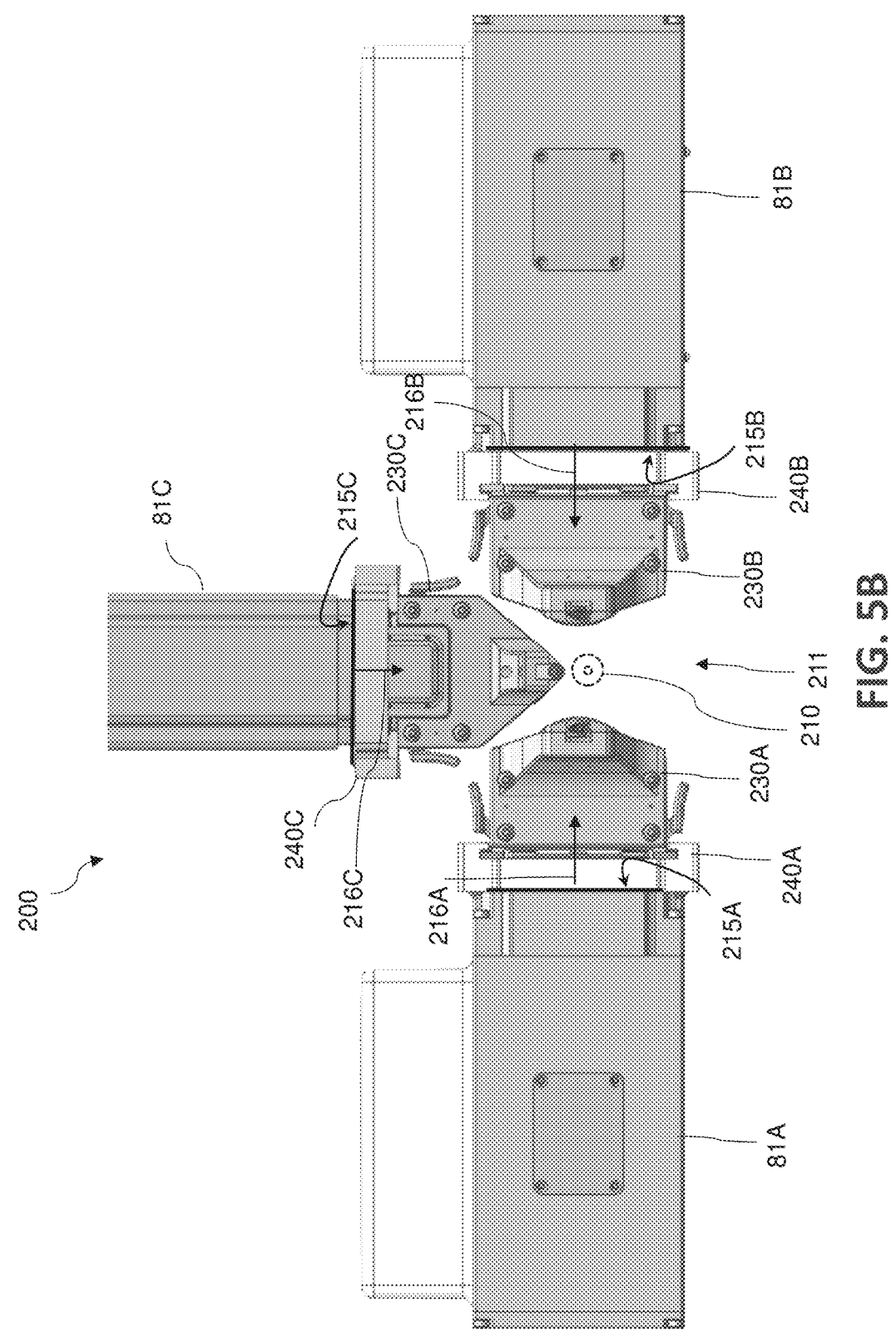
FIG. 5B depicts a front view of a drive assembly of the robotic system having an inverted "T" configuration, drape plates, and mounted cassettes in accordance with some embodiments.
Figure 6A:
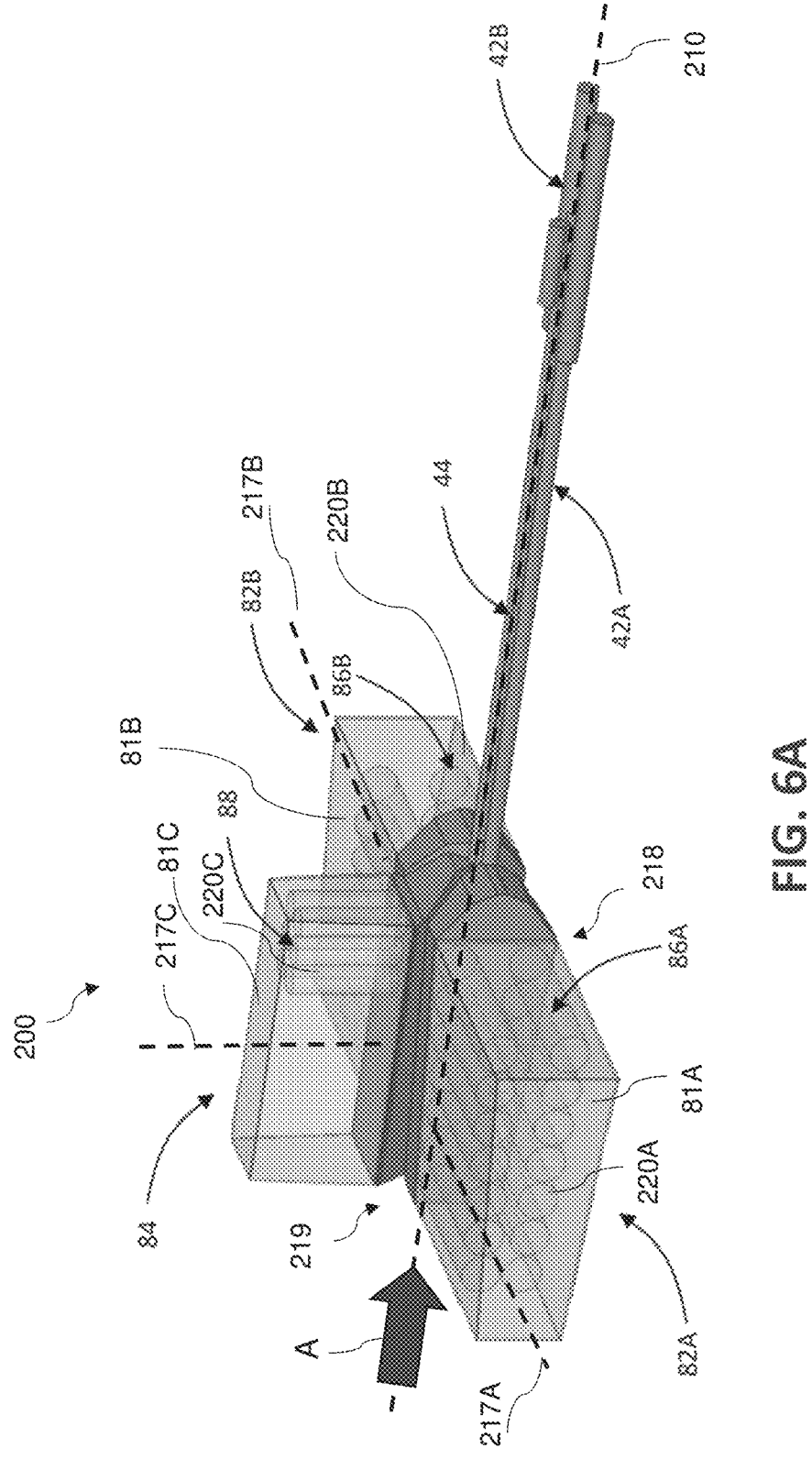
FIG. 6A depicts a perspective view of the drive assembly having an inverted "T" configuration with a lute form factor with cassettes attached thereto of FIG. 5A in accordance with some embodiments.

FIGS. 5A and 6A are a front (patient side) view and a perspective view, respectively of a drive assembly 200 and attached or mounted cassettes 230A, 230B, 230C in accordance with some embodiments. The drive assembly 200 may have a drive assembly common axis 210 (illustrated coming out of the plane of the page) corresponding to a cavity insertion axis during use. FIGS. 5B, 6B, 6C, 6D and 6E are a front (patient side) view, a front perspective view, a side view, a back view and a back perspective view, respectively, of another embodiment of a drive assembly 200, attached drape plates 240A, 240B, and attached or mounted cassettes 230A, 230B, 230C in accordance with some embodiments. FIG. 6F depicts a perspective view of the second drive unit 81B showing the second drive unit face 215B with a frame 241B of a drape plate attached in accordance with some embodiments.

The drive assembly 200 includes a first drive unit 81A, which may be a first arm drive unit. The first drive unit 81A has a first drive unit face 215A with a first vector 216A normal to the first drive unit face 215A. The first drive unit includes a plurality of drive elements (e.g., see drive elements 94B of FIG. 6F-6G, drive elements 94A of FIG. 4, drive-side crown elements 90, 94 of FIGS. 11A and 11D) each having a mating surface 95B. A drive unit face is a surface at which drive elements mate or interface with corresponding elements (e.g., drape plate elements or cassette elements) to transmit torque and drive rotation of the corresponding drape plate elements or cassette elements. In some embodiments, the mating surfaces of the drive elements define a portion of the drive unit face. The first drive unit 81A also includes a plurality of motors 220A, each configured to rotate a corresponding drive element about a different rotation axis 217A perpendicular to, or substantially perpendicular to, the first drive unit face 215A.

The drive assembly 200 also includes a second drive unit 81B, which may be a second arm drive unit. The second drive unit 81B has a second drive unit face 215B with a second vector 216B normal to the second drive unit face 215B and includes a plurality of drive elements each having a mating surface. The second drive unit 81B also includes a plurality of motors 220B, each configured to rotate a corresponding drive element about a different rotation axis 217B.

The drive assembly 200 may also include a third drive unit 81C, which may be a camera drive unit. The third drive unit 81C has a third drive unit face 215C with a third vector 216C normal to the third drive unit face 215C and includes a plurality of drive elements, each having a mating surface. The third drive unit 81C also includes a plurality of third motors 220C each configured to rotate a corresponding third drive element about a different rotation axis 217C perpendicular to, or substantially perpendicular to, the third drive unit face 215C.

The drive assembly 200 may also include the drive assembly common axis 210 corresponding to a cavity insertion axis. The drive assembly 200 may have a vertical plane 251 extending through the drive assembly common axis 210 that is oriented vertically during use.

A positioning of the first drive unit 81A and the second drive unit 81B about the drive assembly common axis 210 may be symmetric with respect to reflection across the vertical plane 251 in some embodiments. The third drive unit 81C may be positioned to be bisected by the vertical plane 251 and to be disposed above the drive assembly common axis 210 during use in some embodiments.

In some embodiments, the first drive unit 81A, the second drive unit 81B, and the third drive unit 81C may be configured to be positioned about the drive assembly common axis 210 with respect to the vertical plane 251 such that an orientation and position of the first drive unit face 215A mirrors an orientation and position of the second drive unit face 215B, and the third drive unit face 215C is bisected by the vertical plane 251.

The first vector 216A, the second vector 216B and the third vector 216C may all lie in a common plane in accordance with some embodiments. In some embodiments, the first drive unit 81A may be configured to be positioned about the drive assembly common axis 210 with the first vector 216A at a first angle 221A relative to the vertical plane 251 as measured in the common plane. The second drive unit 81B may be configured to be positioned about the drive assembly common axis 210 with the second vector 216B at a second angle 221B relative to the vertical plane 251 as measured in the common plane. The second angle 221B may have a same magnitude and opposite sign of those of the first angle 221A in some embodiments. The third drive unit 81C may be configured to be positioned about the drive assembly common axis 210 with the third vector 216C parallel to the vertical plane 251 or lying in the vertical plane 251, and with the third drive unit 81C being positioned above the drive assembly common axis 210 during use.

The first drive unit 81A, the second drive unit 81B, and the third drive unit 81C may be positioned about the drive assembly common axis 210 such that the first vector 216*a*, the second vector 216B, and the third vector 216C are each perpendicular to the drive assembly common axis 210 in accordance with some embodiments.

The first drive unit 81A may be configured to drive a first robotic arm assembly. The second drive unit 81B may be configured to drive a second robotic arm assembly. The third drive unit 81C may be configured to drive a camera assembly in accordance with some embodiments.

In some embodiments, the first drive unit face 215A, the second drive unit face 215B, and the third drive unit face 215C at least partially define a central channel extending through the drive assembly 200 with the drive assembly common axis 210 extending through the central channel.

Figure 6B:
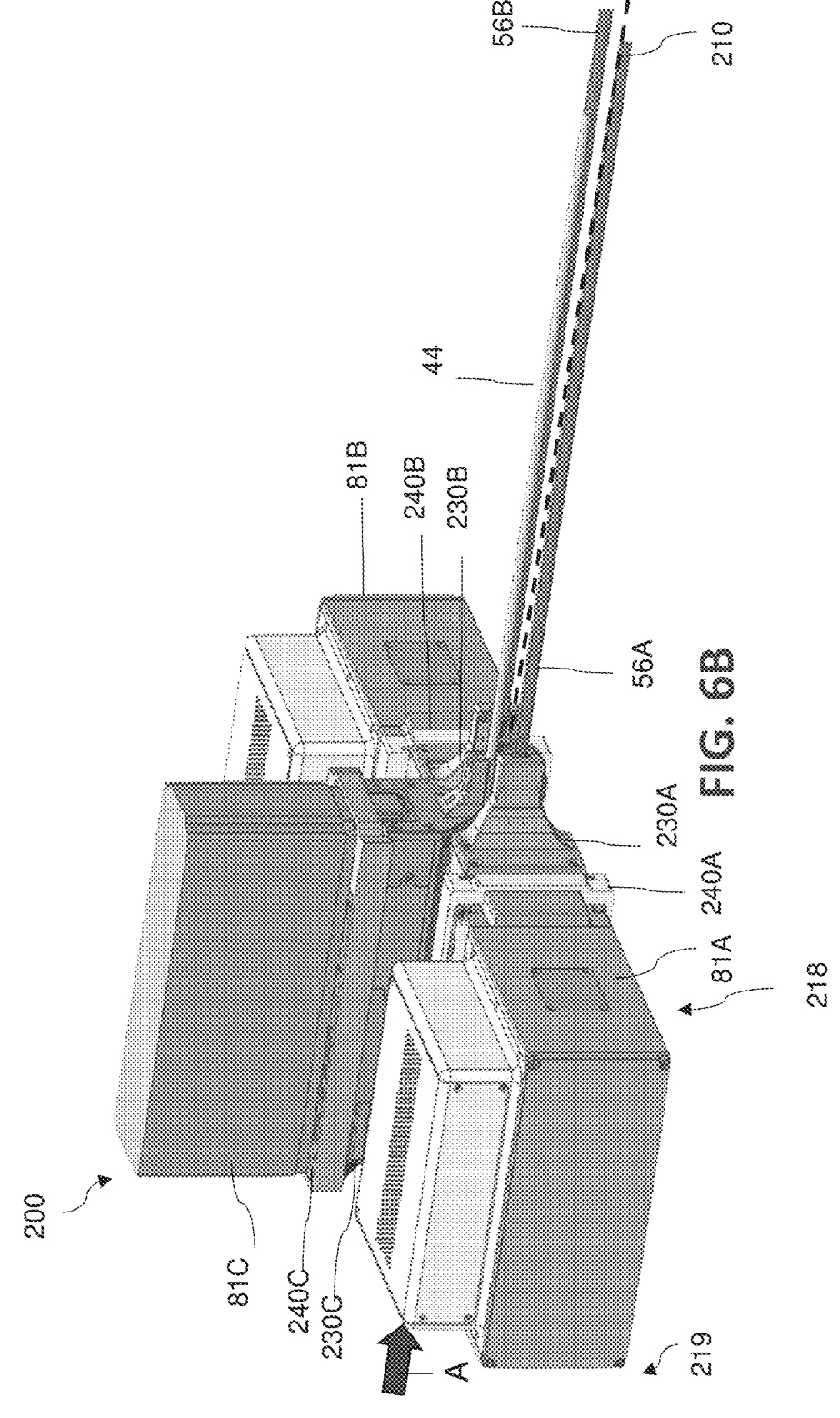
FIG. 6B depicts a perspective view of the drive assembly having an inverted "T" configuration with drape plates and cassettes attached thereto of FIG. 5B in accordance with some embodiments.

The first drive unit 81A, the second drive unit 81B, and the third drive unit 81C may all be positioned within about a 180 degree range about the drive assembly common axis 210 as depicted in FIG. 5A and in FIG. 6B.

The drive assembly 200 in FIGS. 5A and 6A and the drive assembly in FIGS. 5B, 6B, 6C, 6D and 6E both include an inverted T or upside down T shaped configuration, arrangement, or orientation of drive units. In the inverted or upside down T configuration, the first drive unit 81A, the second drive unit 81B, and the third drive unit 81C may be configured to be positioned with the mating surfaces of the plurality of first drive elements facing the mating surfaces of the plurality of second drive elements, with the first drive unit face 215A opposite and parallel to or substantially parallel to the second drive unit face 215B, and with the third drive unit face 215C disposed perpendicularly to or substantially perpendicularly to the first drive unit face 215A as depicted in FIG. 5A and FIG. 5B. In some embodiments, the third drive unit 81C, which may be a camera drive unit, is positioned above the first drive unit 81A and above the second drive unit 81B.

Although the drive assembly embodiments in FIGS. 5A through 6E depict embodiments in which the first drive unit 81A and second drive unit 81B are configured to be positioned and oriented such that the first drive unit face 215A is parallel to the second drive unit face 215B, and such that the angle 221A between first vector 116A normal to the first drive unit face 115A and the vertical plane 251 is 90 degrees, and the angle 221B between the second vector 116B normal to the second drive unit face 115A and the vertical plane is −90 degrees, embodiments are not so limited. For example, in some inverted Y configurations a magnitude of the angles 221A, 221B may be less than 90 degrees (e.g., between 10 degrees and 90 degrees). In some embodiments, a magnitude of the angles 221A, 221B may be more than 90 degrees (e.g., between 90 degrees and 170 degrees).

A drive unit face may not be entirely flat. Descriptions of a drive unit face being substantially parallel to another drive unit face or perpendicular to another drive unit face refer to overall orientations of the drive unit faces. A drive unit face being substantially parallel to another drive unit face, as used herein, refers to an overall orientation of a drive unit face being within 2 degrees of parallel to an overall orientation of another drive unit face. A drive unit face being substantially parallel to another drive unit face, as used herein, refers to an overall orientation of a drive unit face being within 2 degrees of parallel to another drive unit face. A rotation axis of a motor or a rotation axis of a drive element being perpendicular to a drive unit face, as used herein, refers the rotation axis being perpendicular to an overall orientation of the drive unit face. A rotation axis of a motor or a rotation axis of a drive element being substantially perpendicular to a drive unit face, as used herein, refers the rotation axis being within 2 degrees of perpendicular to an overall orientation of the drive unit face.

As noted above, in some embodiments, the first drive unit face 215A, the second drive unit face 215B, and the third drive unit face 215B may at least partially define a central channel 211 through which the drive assembly common axis 210 extends. The first drive unit 81A may be configured to connect with a first cassette 230A in the central channel 211. The second drive unit 81B may be configured to connect with a second cassette 230B in the central channel 211. The third drive unit 81C may be configured to connect with a third cassette 230C in the central channel 211. As explained above, a cassette may be a robotic arm subassembly or a camera subassembly, or a portion of a robotic arm subassembly or camera subassembly in accordance with some embodiments. The first cassette 230A may be a first robotic arm subassembly (e.g., robotic arm subassembly 56 of FIG. 2A) or a portion of a first robotic arm subassembly, the second cassette 230B may be a second robotic arm subassembly or a portion of a second robotic arm subassembly, and the third cassette 230C may be a camera assembly (e.g., camera arm subassembly 78 of FIG. 2B). The first arm subassembly, the second arm subassembly, and the camera sub assembly may be configured for insertion via a single trocar (e.g., by arrangement along the central channel 211 and drive assembly common axis 210).

In some embodiments a sterile drape plate is installed onto a drive unit face of each of the drive units. The drape plate acts as a sterile barrier between the nonsterile equipment and the sterile cassettes and provides interfaces to transmit torque from the drive motors to the cassettes. In some embodiments, the drape plate also provides alignment and attachment features to both the drive unit faces and the cassettes.

In some embodiments, the first drive unit 81A may be configured to connect with the first cassette 230A via a first drape plate 240A (see, e.g., FIGS. 5B, 6B, 6C, 6D and 6E). The second drive unit 81B may be configured to connect with the second cassette 230B via a second drape plate 240B. The third drive unit 81C may be configured to connect with the third cassette 230C via a third drape plate 240C.

In some embodiments, the first cassette 230A may be a first robotic arm assembly, the second cassette 230B may be a second robotic arm assembly, and the third cassette 230C may be a camera assembly. The first arm assembly, the second arm assembly, and the camera assembly may be configured for insertion via a single trocar (e.g., by arrangement along the central channel 211 and drive assembly common axis 210).

In some embodiments, the first drive unit is configured to connect with an interface portion of the first cassette inserted into the central channel. FIG. 5B illustrates another embodiment of a drive assembly 200 including a first drive unit 81A, a second drive unit 81B, and a third drive unit 81C. A first cassette 230A is slidably mounted to the first drive unit 81A via a drape plate 240A. A second cassette 230B is slidably mounted to the second drive unit 81B via a drape plate 240B. A third cassette 230C is slidably mounted to the third drive unit 81C via a drape plate 240C.

In some embodiments first drive unit 81A may be configured to connect with the first cassette 230A at the first drive unit face 215A. The second drive unit 81B may be configured to connect with the second cassette 230B at the second drive unit face 215B. The third drive unit 81C may be configured to connect with the third cassette 230C at the third drive unit face 215C.

The first drive unit 81A may be configured for the first cassette 230A to be slidably received by displacing the first cassette 230A with respect to the first drive unit 81A in a plane parallel to the first drive unit face 215A and parallel to the drive assembly common axis 210. The first drive unit 81A may be configured to drive a first robotic arm assembly (robot arm 42A). The second drive unit 81B may be configured to drive a second robotic arm assembly (robot arm 42B). The third drive unit 81C may be configured to drive a camera assembly 84. The second drive unit 81B may be configured for the second cassette 230B to be slidably received by displacing the second cassette 230B with respect to the second drive unit 81B in a plane parallel to the second drive unit face 215B and parallel to the drive assembly common axis 210. The third drive unit 81C may be configured for the third cassette 230C to be slidably received by displacing the third cassette 230C with respect to the third drive unit 81C in a plane parallel to the third drive unit face 215C.

FIG. 6A illustrates the drive assembly 200 with the first drive unit 81A including a plurality of first motors 220A, the second drive unit 81B including a plurality of second motors

220B, and the third drive unit 81C including a plurality of third motors 220C. Each of the first motors 220A may have a drive shaft perpendicular to the first drive unit face 215A and parallel to the first vector 216A. Each of the second motors 220B may have a drive shaft perpendicular to the second drive unit face 215B and parallel to the second vector 216B. Each of the third motors 220C may have a drive shaft perpendicular to the third drive unit face 215C and parallel to the third vector 216C.

FIG. 6B illustrates the drive assembly 200 with the first drive unit 81A mounted with the first cassette 230A via the first drape plate 240A, the second drive unit 81B mounted with the second cassette 230B via the first drape plate 240B, and the third drive unit 81C mounted with the third cassette 230C via the third drape plate 240C. The first drape plate 240A is configured to be disposed between the first drive unit 81A and the first cassette 230A. The second drape plate 240B configured to be disposed between the second drive unit 81B and the second cassette 230B. The third drape plate 81C is configured to be disposed between the third drive unit 81C and the third cassette 230C. The first cassette 230A may be a first robotic arm assembly with robot arms 42A. The second cassette 230B may be a second robotic arm assembly with robot arms 42B, and the third cassette 230C may be a camera assembly 44. The first arm assembly, the second arm assembly, and the camera assembly may be configured for insertion via a single trocar.

Figures 6C, 6D:
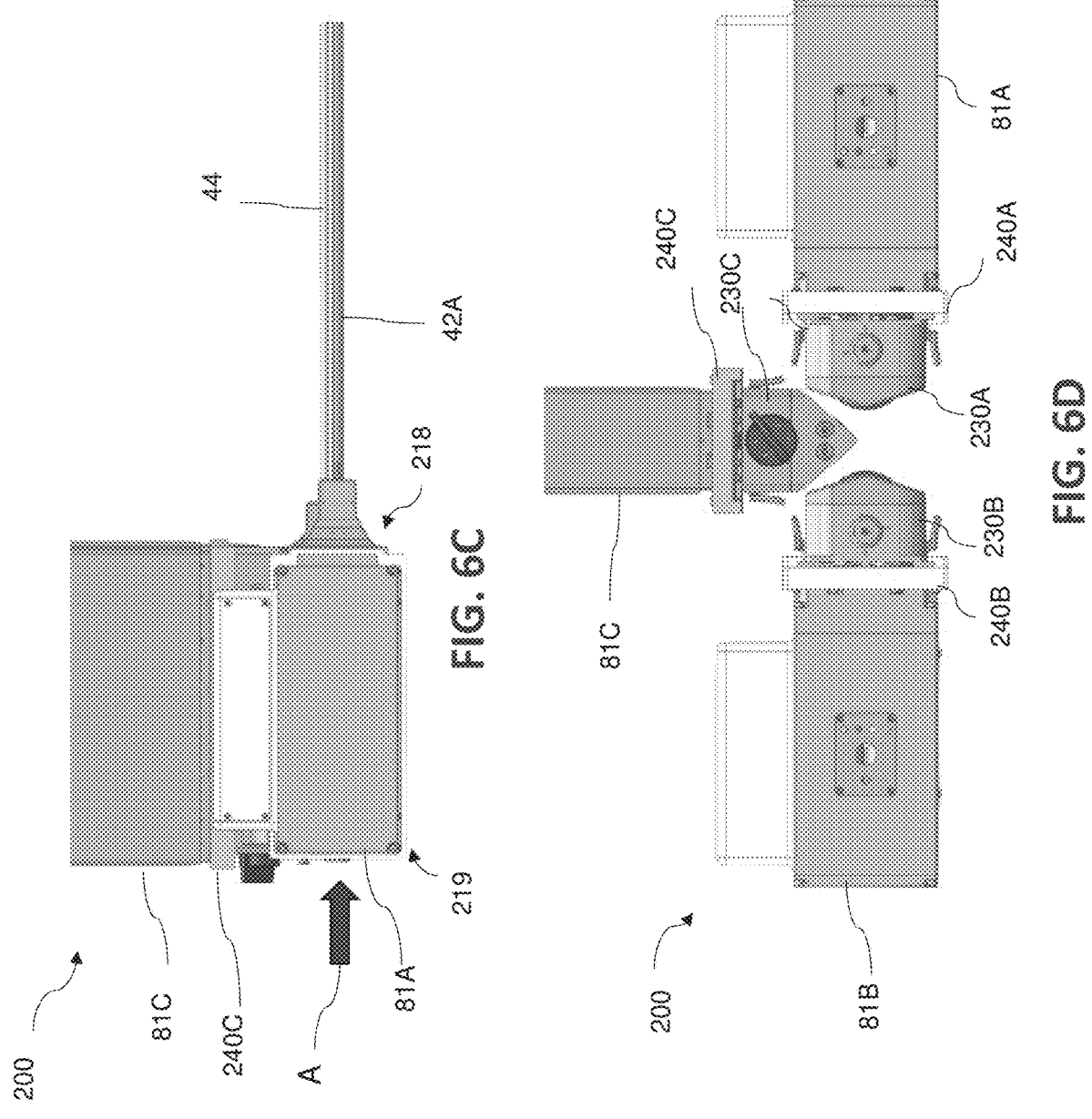
FIG. 6C depicts a side view of the drive assembly having an inverted "T" configuration with drape plates and cassettes attached thereto of FIG. 5B in accordance with some embodiments.
FIG. 6D depicts a back view of the drive assembly having an inverted "T" configuration with drape plates and cassettes attached thereto of FIG. 5B in accordance with some embodiments.
Figure 6E:
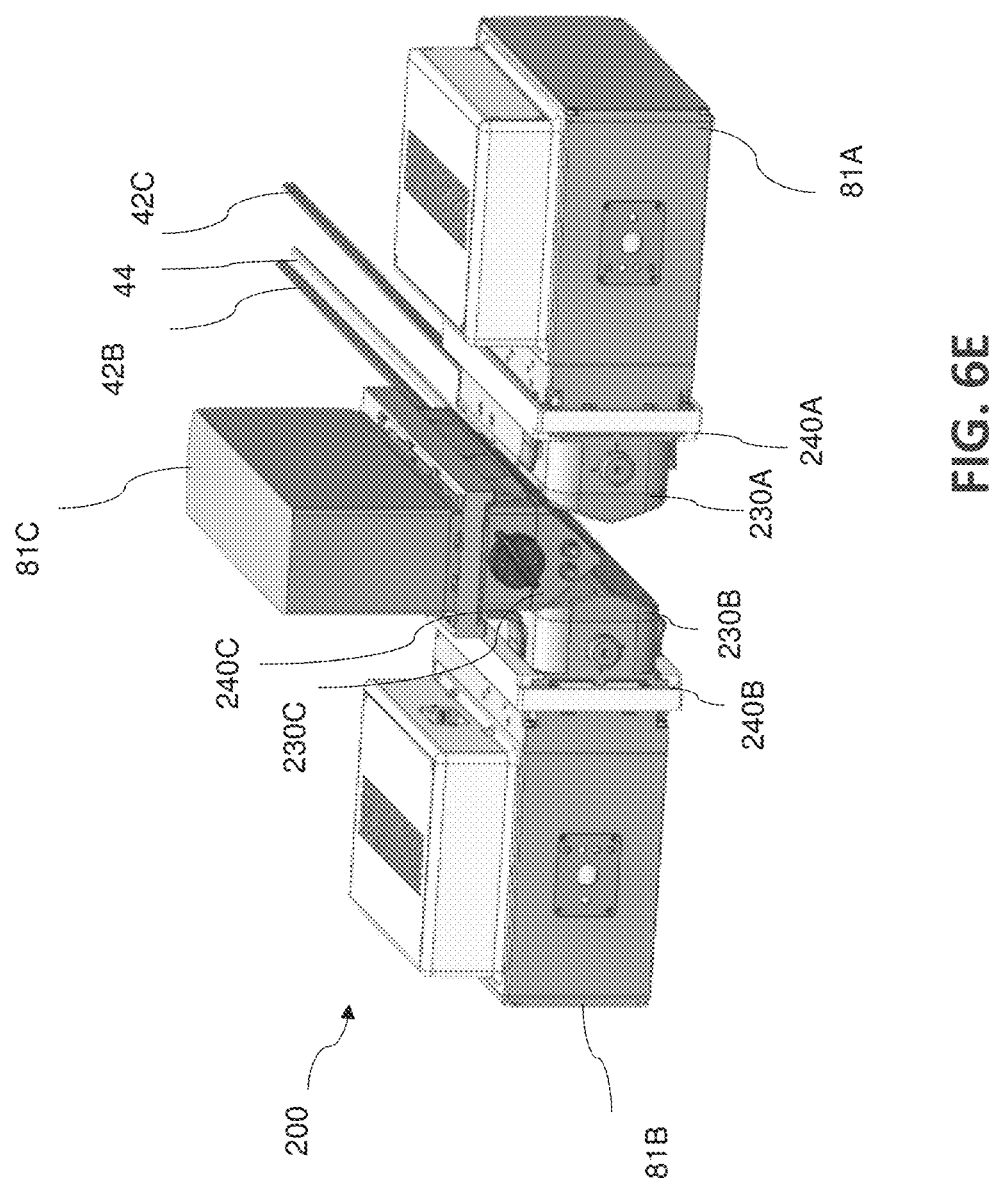
FIG. 6E depicts a rear perspective view of a drive assembly having an inverted "T" configuration with drape plates and cassettes attached thereto of FIG. 5B in accordance with some embodiments.
Figure 6F:
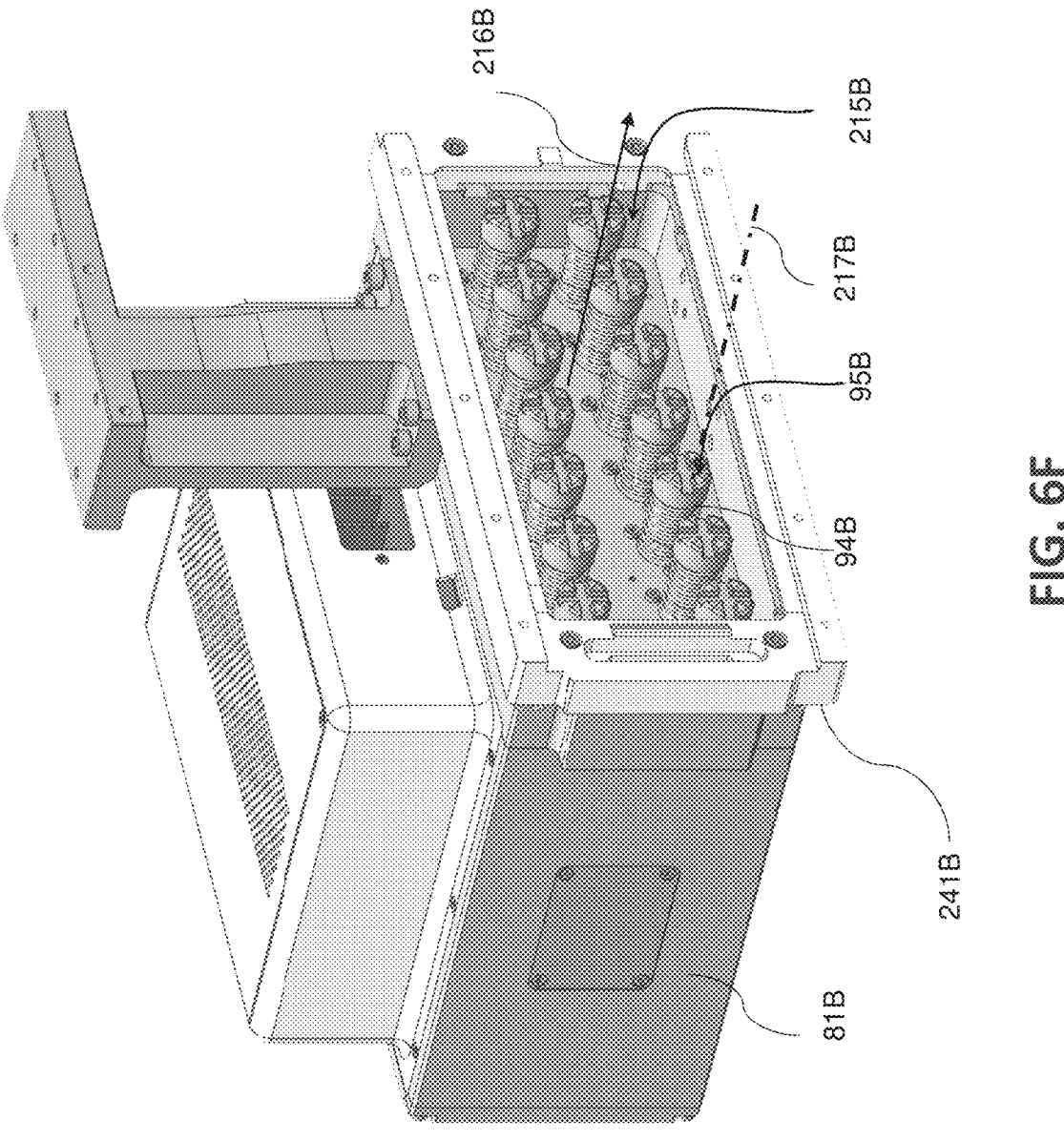
FIG. 6F depicts a perspective view of the second drive unit showing the second drive unit face with a frame of a drape plate attached in accordance with some embodiments.
Figure 6G:
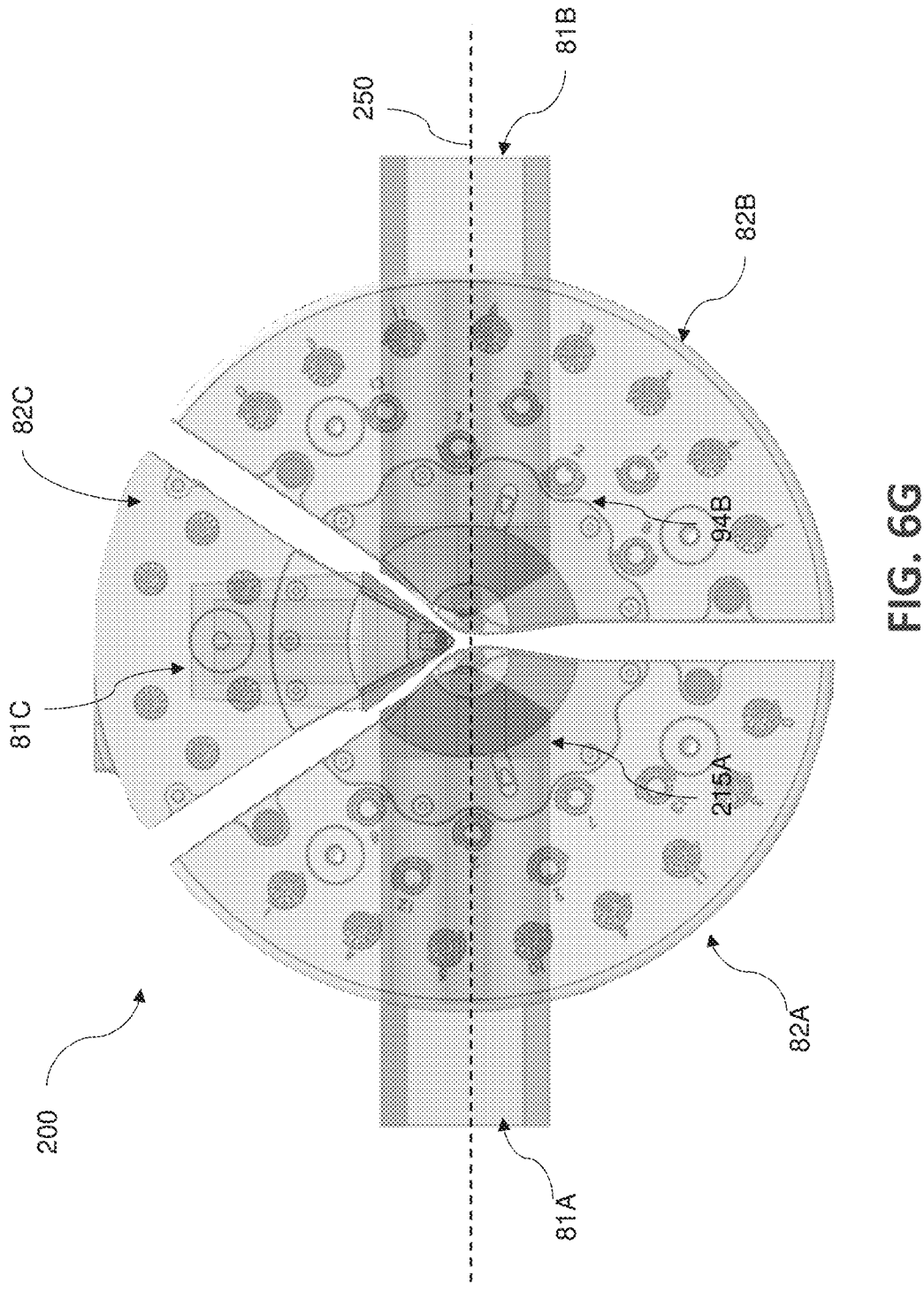
FIG. 6G depicts the inverted T form factor drive assembly of FIG. 5A overlaying the drum form factor drive assembly of FIG. 4 in accordance with some embodiments.

The drive assembly 200 may have a front end 218, also referred to herein as a distal end, configured to be closer to the patient in use, and a back end 219, also referred to herein as a proximal end, configured to be further from the patient in use as illustrated in FIGS. 6A-6C. In some embodiments, to install cassettes 230A, 230B (e.g., robot arm subassemblies 56 of FIG. 4) into the drive units 81A and 81B, the cassettes 230A, 230B are moved or slid in the with respect to the drive assembly 200 in the direction of arrow A into the central channel via the back end 219 of the drive assembly, as shown in FIGS. 6A-6C, 7A, and 7. Similarly, to install the camera assembly 44 into the camera drive unit 81A, 81B, the cassette 230C camera assembly 44 is slid in the direction of arrow A, as shown in FIGS. 6A-6C, 7A and 7B, onto an inner face of the camera drive unit 84 from the back of the camera drive unit 84. In this embodiment, the motors of each drive unit are arranged pointing towards the center of the three drive units. While the upside down T form factor assembly configuration is wider than the drum form factor drive assembly configuration, the upside down T form factor assembly configuration lesser distance below the cavity insertion axis or the midplane 250 of the trocar, which decreases the chances of the drive units colliding with the patient anatomy or the surgical table and may increase a working space. This is illustrated by FIG. 6G that depicts a front view of the drum form factor drive assembly 200 of FIG. 4 overlaying the inverted T form factor drive assembly 200 of FIG. 5A in accordance with some embodiments.

The first drive unit 81A may be configured to connect with an interface portion of the first cassette 230A inserted into the central channel 211 via the back end 219 of the drive assembly 200 in a first direction parallel to the drive assembly common axis 210. The second drive unit 81B may be configured to connect with an interface portion of the second cassette 230B inserted into the central channel 211 via the back end of the drive assembly 219 in a second direction parallel to the drive assembly common axis 210. The third drive unit 81C may be configured to connect with an interface portion of the third cassette 230C inserted into the central channel 211 from the back end 219 of the drive assembly 200.

The first drive unit 81A may be configured to slidably receive the interface portion of the first cassette 230A inserted into the central channel 211 from the back end 219 of the drive assembly 200 in a direction indicated by arrow A. The second drive unit 81B may be configured to slidably receive the interface portion of the second cassette 230B inserted into the central channel 211 from the back end 219 of the drive assembly 200. The third drive unit 81C may be configured to slidably receive an interface portion of the third cassette 230C inserted into the central channel 211 from the back end 219 of the drive assembly 200 in a third direction parallel to the drive assembly common axis 210.

Figure 7B:
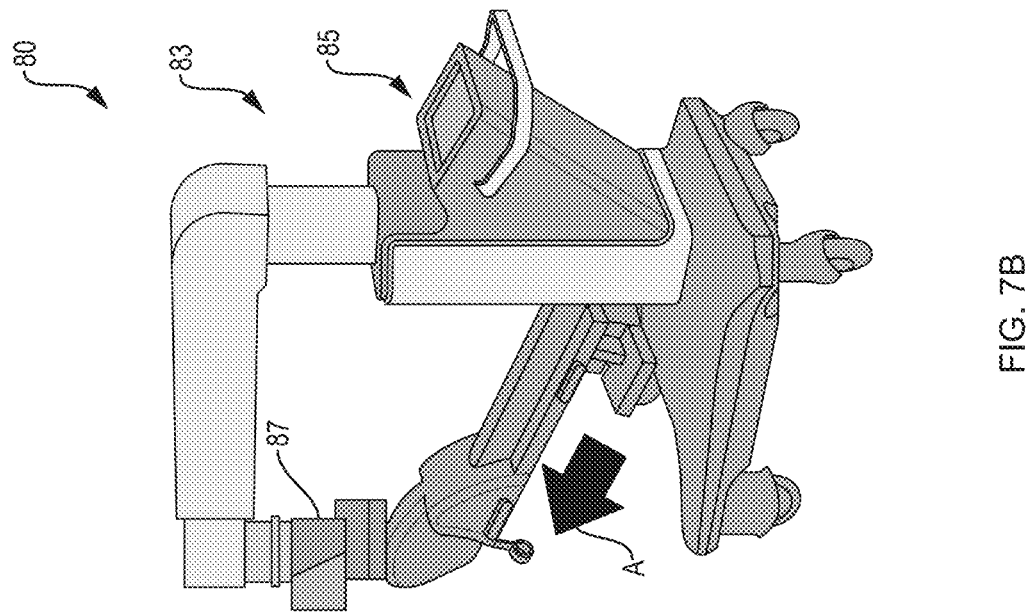
FIG. 7B is a rear perspective view of the patient cart of the surgical robotic system with a drive assembly having an inverted "T" configuration and lute form factor of FIG. 7A in accordance with some embodiments.
Figure 7A:
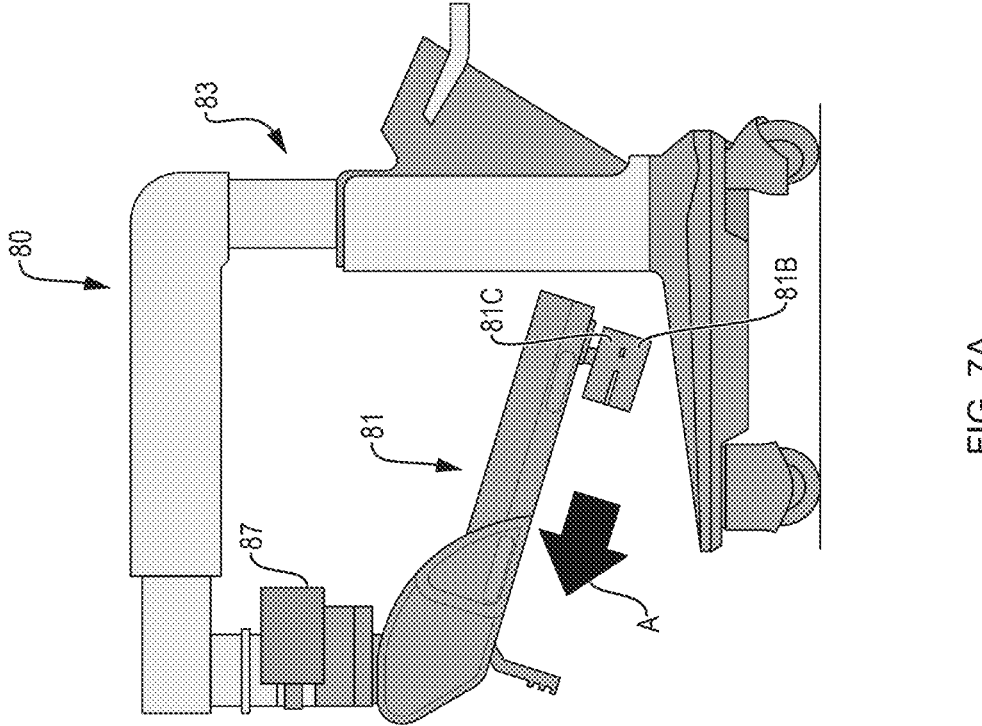
FIG. 7A is a side view of a patient cart of a surgical robotic system with a drive assembly having an inverted "T" configuration and lute form factor in accordance with some embodiments.

With particular reference to FIGS. 7A and 7B, in one embodiment, the RSS 80 is a mobile patient cart 80. As depicted in FIGS. 7A and 7B, the patient cart 80 includes a platform with a plurality of wheels that enable movement of the patient cart 80. The patient cart 80 also includes and an arm 81 that supports the drive units 81A, 81B and 81C and a support member 83 that connects the arm 81 to the platform. The support member 83 may move vertically and the arm 81 may move horizontally to align the drive units 81A, 81B and 81C (and therefore cassettes attached thereto) with a region to be operated on. Furthermore, the angle of the arm 81 with respect to the support member 83 may also be adjusted to align the drive units 81A, 81B and 81C and attached cassettes with the region to be operated on. As further depicted in FIGS. 7A and 7B, the patient cart 80 includes a control unit 85 for moving the arm 81 and support member 83 as previously discussed and a display 87 that is connected to and in communication the camera assembly 44 when the camera assembly 44 is installed in the camera drive assembly 84. The display 87 may provide a livestream of an operation as captured by the camera assembly 44 in some embodiments.

Figure 8:
FIG. 8 is a side view of a drive stack up including a motor with an attached spool and pulley assembly in accordance with some embodiments.
Figure 9:
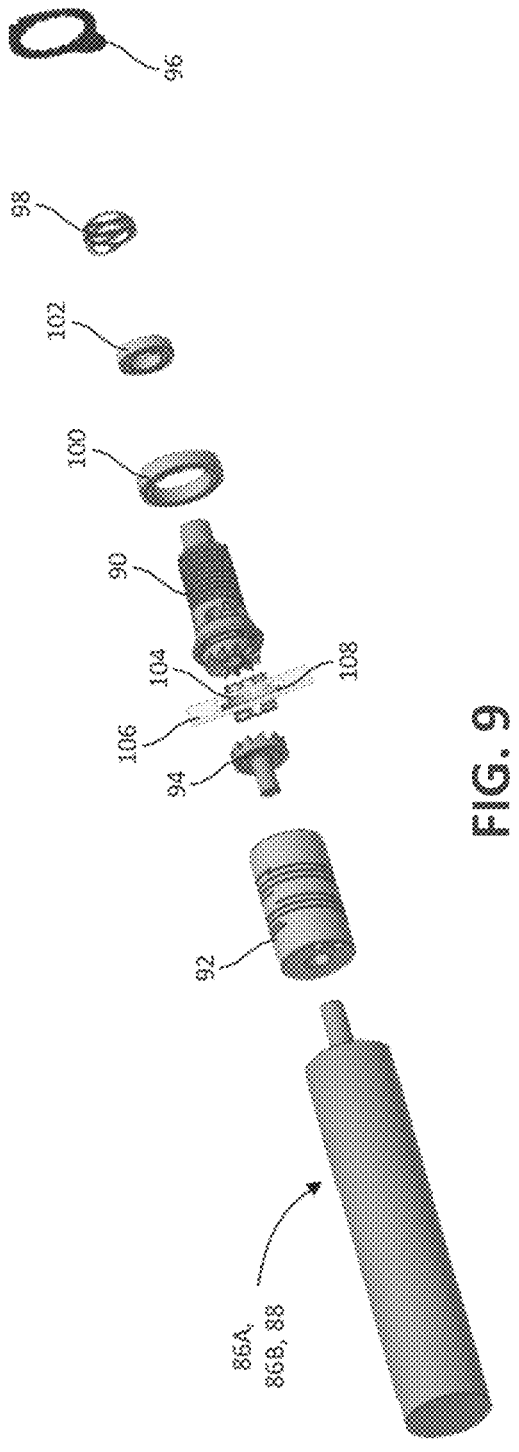
FIG. 9 is an exploded perspective view of the drive stack up including the motor and the spool and pulley assembly of FIG. 8 in accordance with some embodiments.

As described herein, movement of the robotic arms 42A and 42B and the camera assembly 44 can be cable driven. As shown in FIGS. 8 and 9, each of the motors in each of the drive units can be connected to a corresponding spool and pulley (hereinafter referred to as a "spooley") assembly 90 at an interface region formed between the motors of the drive units and a connected interface housing of the robot arms and camera assembly. In embodiments incorporating a drape plate, each of the motors in each of the drive units can be connected to a corresponding spool and pulley assembly 90 at an interface region formed between the motors of the drive units, drape plate elements (e.g., intermediate drape discs housed in the drape plate) and a connected interface housing of the robot arms and camera assembly. The spooley assembly 90 is disposed within the interface housing and is connected to the motors via a suitable motor coupling 92. In some embodiments, a spooley assembly is connected to a motor via an intermediate drape disc, a drive element such as a crown, and a motor coupling, The coupling 92 is flexible in order to accommodate misalignment. A cable (not shown) that drives movement of the robot arms or the camera assembly is wound around an outer portion of the spooley assembly 90. In the illustrated embodiment, the spooley assembly 90 has a helical groove formed along the outer surface. The cable can be tensioned when the spooley assembly 90 is turned in a given direction by the motor of the corresponding drive element via a torque transmission feature. For example, according to one embodiment, the torque transmission feature can include a crown feature integrally formed at one end of the spooley assembly 90 and which connects to a drive-side crown element 94. Crown features as described herein include a male spline extending from a circular surface. Each male spline is adjacent to a female spline. A male spline of one element is configured to mate with a female spline of another element and thus provide for the transmission of mechanical power in the form of torque. While the spooley assembly 90 and the drive-side crown element 94 are described as including crown features, in other embodiments the spooley assembly 90 and the drive-side crown element 94 may include other features that allow the spooley assembly 90 and the drive-side crown element 94 to connect and transmit mechanical power. The drive-side crown element 94 can be a standalone element that is held by a flexible shaft coupling and which is clamped onto the shaft of the motor. This torque transmission feature transmits torque needed to turn the spooley assembly 90 in a desired direction. A brake plate 96 can be employed to engage with teeth formed on the spooley assembly 90 to constrain rotation thereof. A spring element 98 provides an axial compliance and serves to bias the spooley assembly 90 towards the brake plate 96, which keeps the brake plate 96 engaged with the spooley assembly 90 when the interface housing is detached from the motor. As the interface housing is installed onto the drive element, the spooley assembly 90 is depressed, which disengages the spooley assembly 90 from the brake plate 96, thereby allowing the spooley assembly 90 to freely rotate. A top bearing 100 and a bottom bearing 102 are also coupled to the spooley assembly 90.

In some embodiments the drive unit 81A also includes a plurality of motor couplings 92, each motor coupling 92 connecting a drive-side crown element 94 to a corresponding motor 86 to rotate the drive-side crown element 94. Each motor coupling 92 may enable the corresponding first drive-side crown element 94 to displace with respect to the first motor 86 to provide compliance for mating with the first drive-side crown element 94.

In some embodiments, the plurality of drive elements 82A may include a plurality of drive-side crown elements 94. The robotic subsystem may include a first cassette 230A including a plurality of first spooley assemblies 90, each first spooley assembly 90 including a spool and a pulley and configured to be driven by the corresponding first drive-side crown element 94.

The robotic subsystem may further include a first drape plate 104, which may have a plurality of intermediate disks 108, configured to be disposed between the first drive unit 81A and the first cassette 230A. The robotic subsystem may further include a second drape plate 104', which may have a plurality of intermediate disks 108, configured to be disposed between the second drive unit 81B and the second cassette 230B. The robotic subsystem may further include a third drape plate 104", which may have a plurality of intermediate disks 108, configured to be disposed between the third drive unit 81B and the third cassette 230C.

Figure 10:
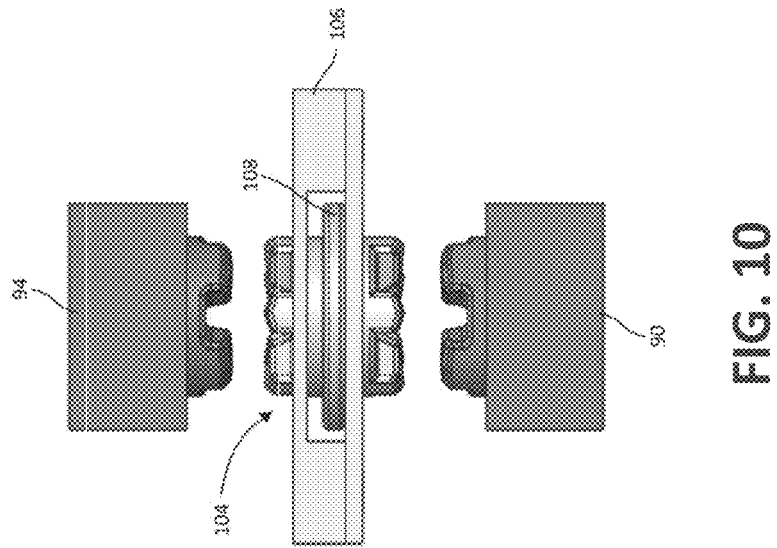
FIG. 10 is a side view of a crown of a spool and pulley assembly, a drive-side crown, and a drape plate in accordance with some embodiments.

As is known in the art, in order to isolate the patient cart from the patient during surgery, a drape or covering can be employed to cover the patient cart to provide a sterile barrier. Since the drape forms a barrier between the robotic unit and the drive units, a mechanical connection needs to be formed in the drape to allow for mechanical interaction between the drive units and the robotic unit. As shown in FIGS. 9 and 10, a drape plate 104 can be disposed between the drive side-crown 94 on the drive unit side of the drape and the spooley assembly 90 provided on the robotic unit side of the drape. Opposing outer surfaces of the drape plate 104 can have mechanical connection features (e.g., corresponding crown features) extending therefrom which allow the drape plate 104 to mate with the drive units on one side and with the robotic unit on the opposed side.

According to some embodiments, the drape plate 104 can include a housing having a first crown feature formed on a drive face or side of the housing and a second crown feature formed on an instrument side or face that is opposite the motor face. The crown features formed on the motor face engage with drive-side crown 94 and the crown features on the opposed instrument side engage with the crown feature of the spooley assembly 90. In other words, the spooley assembly 90 and the drive-side crown 94 are each formed in a shape that mates with respective sides of the drape plate 104. Notably, the present disclosure is not limited to a crown shape and other shapes capable of mating are contemplated. A sterile film 106 can be sealed to the drape plate 104, thereby providing a sterile environment on a patient side of the surgical robotic system 10. The drape plate 104 further includes an intermediate disk 108 mounted within the housing and which is coupled to the crown features. The intermediate disk 108 is able to rotate and has a small amount of radial play while also maintaining a sufficiently tortuous path required to maintain sterility. The intermediate disk 108 includes torque transmission features on each side similar to the crown features of the drape plate 104.

Figures 11A, 11B, 11C, 11D:
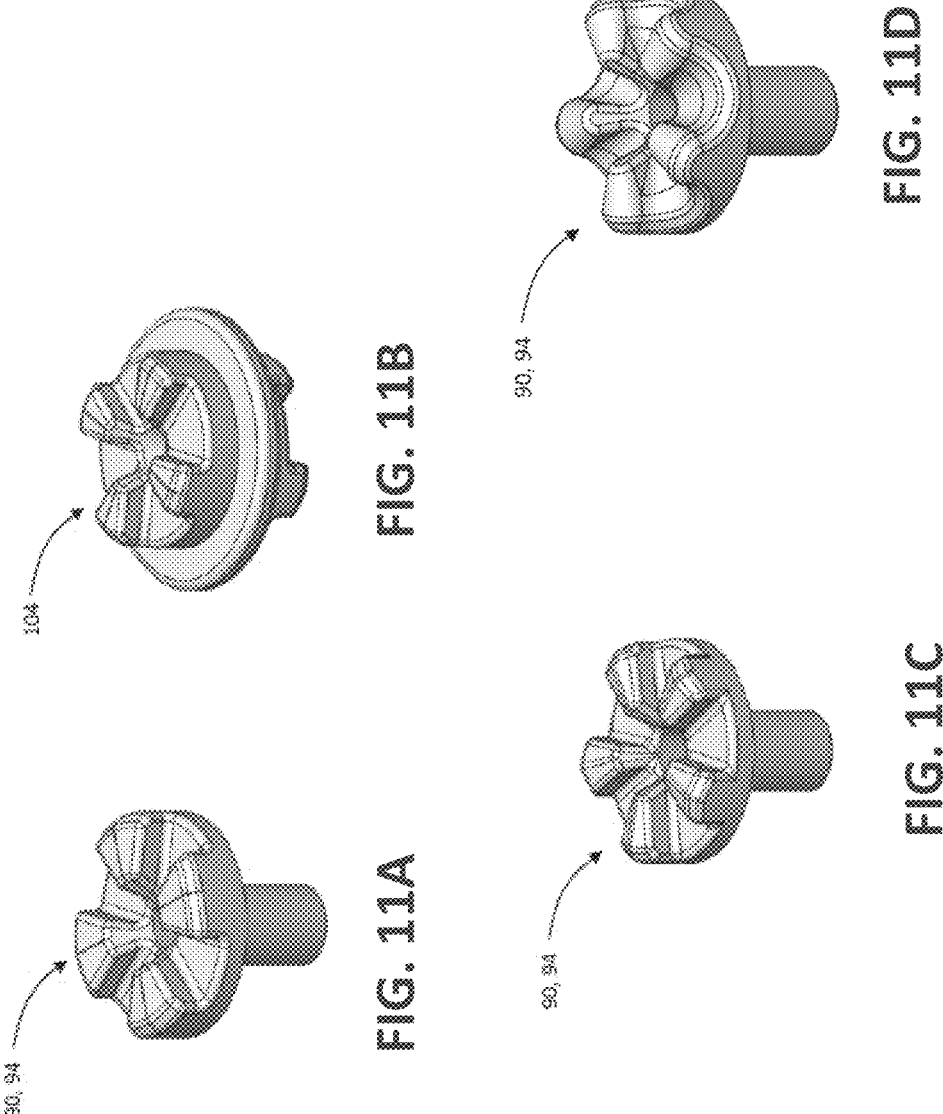
FIG. 11A is a perspective view of a mating surface configuration for a drive-side crown or a spooley in accordance with an embodiment.
FIG. 11B is a perspective view of a mating surface configuration for a drape plate mating element 104 in accordance with an embodiment.
FIG. 11C is a perspective view of a mating surface configuration for a drive-side crown or a spooley in accordance with another embodiment.
FIG. 11D is a perspective view of a mating surface configuration for a drape plate mating element 104 in accordance with an embodiment.

With reference to FIGS. 11A-11D, the crown features (also referred to as torque transmission features) of the spooley assembly 90, the drive-side crown 94, and the drape plate mating element 104 may have various shapes and configurations. In some embodiments, as shown in FIGS. 11A, and 11B the crown features are symmetric. In some embodiments, as shown in FIGS. 11C and 11D, the crown features are asymmetric. Furthermore, the spooley assembly 90, the drive-side crown 94, and the drape plate mating element 104 may be removably connected to one another such that a different spooley assembly 90, a different drive-side crown 94, and/or a different drape plate mating element 104 with different crown features may be installed. The installation action may be push-on, slide-on, or a combination thereof.

Figure 12:
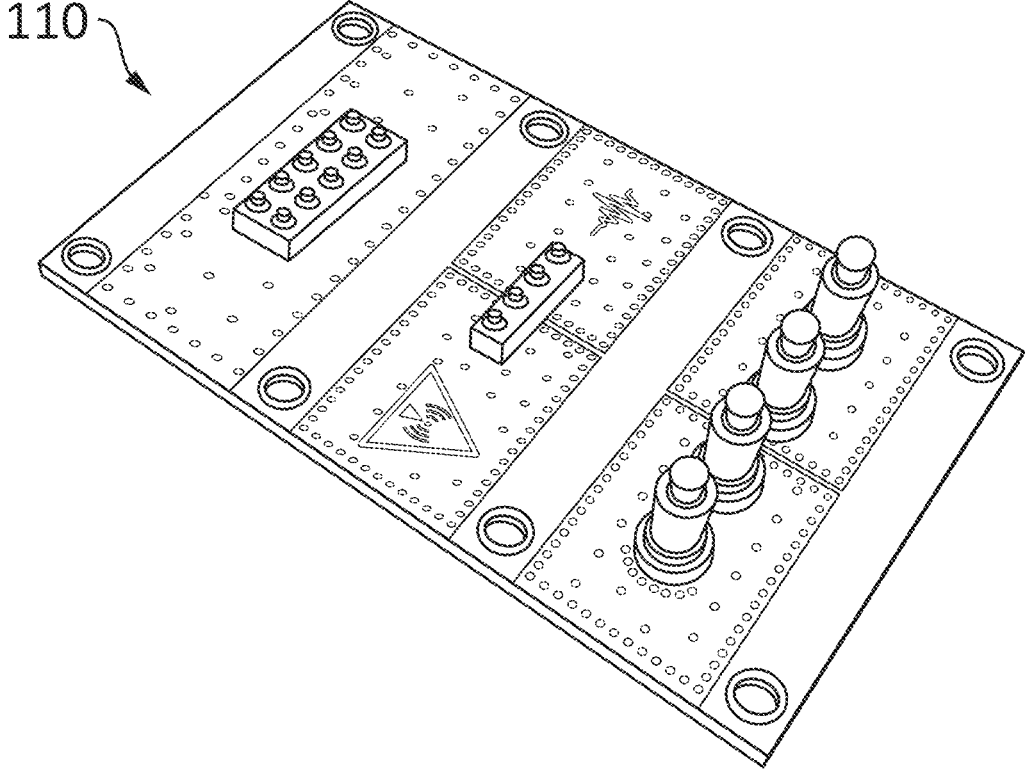
FIG. 12 is an image of a disposable interface board incorporated into some embodiments.

The spooley assembly 90 and the drive-side crown 94 may each include a disposable interface board (DIB) 110 (FIG. 12) for providing an electrical connection between the drive units and the robotic unit. The DIB 110 includes pogo-pin style connectors that extend from the DIB 110. When disposed within the spooley assembly 90 and the drive-side crown 94 these pogo-pin style connectors extend beyond the spooley assembly 90 and the drive-side crown 94. In these embodiments, the drape plate 104 includes a copper pad or pass-through board (e.g., disposed on the intermediate disk 108) that extends between opposite surfaces of the drape plate 104. When a cassette is installed in a drive element, the pogo-style pins of a DIB 110 of a spooley assembly 90 and the pogo-style pins of a DIB 110 of a drive-side crown 94 contact the copper pad of the drape plate 104 which provides an electrical connection between the two DIBs 110. The connection between DIBs 110 allows hall effect data, and cassette tunings to be transmitted between the drives and cassettes. In some embodiments, a separate set of coaxial connectors transmits camera data between the cassette and the drive units. Notably, the present disclosure is not limited to pogo-style pins and other electrical connections between the components are contemplated.

What is claimed is:

1. A drive assembly of a surgical robotic system comprising:

a first drive unit having:
  a first drive unit face;
  a plurality of first drive elements; and
  a plurality of first motors each configured to rotate a corresponding one of the plurality of first drive elements about an axis perpendicular to the first drive unit face;
a second drive unit having:
  a second drive unit face;
  a plurality of second drive elements; and
  a plurality of second motors each configured to rotate a corresponding one of the plurality of second drive elements about an axis perpendicular to the second drive unit face;
a third drive unit having:
  a third drive unit face;
  a plurality of third drive elements; and
  a plurality of third motors each configured to rotate a corresponding one of the plurality of third drive elements about a rotation axis perpendicular to the third drive unit face; and
a drive assembly common axis corresponding to a cavity insertion axis, the first drive unit, the second drive unit, and the third drive unit configured to be positioned about the drive assembly common axis with respect to a vertical plane passing through the drive assembly common axis such that an orientation and position of the first drive unit face mirrors an orientation and position of the second drive unit face and the first drive unit face is opposite and substantially parallel to the second drive unit face, and the third drive unit face is bisected by the vertical plane and is substantially perpendicular to the first drive unit face.

2. The drive assembly of claim 1, wherein the first drive unit is configured to drive a first robotic arm assembly, wherein the second drive unit is configured to drive a second robotic arm assembly, and wherein the third drive unit is configured to drive a camera assembly.

3. The drive assembly of claim 1, wherein each of the plurality of first motors has a drive shaft perpendicular to the first drive face, each of the plurality of second motors has a drive shaft perpendicular to the second drive face, and each of the plurality of third motors has a drive shaft perpendicular to the third drive face.

4. The drive assembly of claim 1, wherein the plurality of first drive elements comprises a plurality of first drive-side crown elements, the plurality of second drive elements comprises a plurality of second drive-side crown elements, and the plurality of third drive elements comprises a plurality of third drive-side crown elements.

5. The drive assembly of claim 4, wherein a mating surface of each of the first drive-side crown elements, a mating surface of each of the second drive-side crown elements, and a mating surface of each the third drive-side crown elements is configured to engage a mating surface of a corresponding element of a drape plate to transmit rotational motion of the drive-side crown element to the corresponding element of the draft plate.

6. The drive assembly of claim 4, wherein the first drive unit further comprises a plurality of first motor couplings, each first motor coupling connecting one of the plurality of first drive-side crown elements to a corresponding one of the plurality of first motors to rotate the one of the plurality of first drive-side crown elements, each of the plurality of first motor couplings enabling the corresponding one of the plurality of drive-side crown elements to displace with respect to the corresponding one of the plurality of first motors to provide compliance for mating with the drive-side crown element.

7. The drive assembly of claim 1, wherein the first drive unit face, the second drive unit face, and the third unit face define a central channel through which the drive assembly common axis extends.

8. The drive assembly of claim 6, wherein the first drive unit is configured to connect with a first cassette in the central channel;

wherein the second drive unit is configured to connect with a second cassette in the central channel; and wherein the third drive unit is configured to connect with a third cassette in the central channel.

9. The drive assembly of claim 8, wherein the first drive unit is configured to connect with the first cassette via a first drape plate;

wherein the second drive unit is configured to connect with the second cassette via a second drape plate; and wherein the third drive unit is configured to connect with the third cassette via a third drape plate.

10. The drive assembly of claim 8, wherein the first drive unit is configured to connect with the first cassette at the first drive unit face;

wherein the second drive unit is configured to connect with the second cassette at the second drive unit face; and wherein the third drive unit is configured to connect with the third cassette at the third drive unit face.

11. The drive assembly of claim 10, wherein the first drive unit is configured to connect with the first cassette via a first drape plate disposed between the first drive unit face and the first cassette;

wherein the second drive unit is configured to connect with the second cassette via a second drape plate disposed between the second drive unit face and the second cassette; and wherein the third drive unit is configured to connect with the third cassette via a third drape plate disposed between third drive unit face and the third cassette.

12. The drive assembly of claim 9, wherein the drive assembly has a front end configured to be closer to a patient in use and a back end configured to be further from the patient in use; and wherein the first drive unit is configured to connect with an interface portion of the first cassette inserted into the central channel from the back end of the drive assembly;

wherein the second drive unit is configured to connect with an interface portion of the second cassette inserted into the central channel from the back end of the drive assembly; and wherein the third drive unit is configured to connect with an interface portion of the third cassette inserted into the central channel from the back end of the drive assembly.

13. The drive assembly of claim 12, wherein the first drive unit is configured to slidably receive the interface portion of the first cassette inserted into the central channel from the back end of the drive assembly in a first direction parallel to the drive assembly common axis;

wherein the second drive unit is configured to slidably receive the interface portion of the second cassette inserted into the central channel from the back end of the drive assembly in a second direction parallel to the drive assembly common axis; and wherein the third drive unit is configured to slidably receive an interface portion of the third cassette inserted into the central channel from the back end of the drive assembly in a third direction parallel to the drive assembly common axis.

14. A robotic subsystem for a surgical robotic system, the robotic subsystem comprising:

a drive assembly according to claim 1, wherein the plurality of first drive elements comprises a plurality of first drive-side crown elements, the plurality of second drive elements comprises a plurality of second drive-side crown elements, and the plurality of third drive elements comprises a plurality of third drive-side crown elements;

a first cassette including a plurality of first spooley assemblies, each of the plurality of first spooley assemblies including a spool and a pulley and configured to be driven by a corresponding one of the plurality of first drive-side crown elements;

a second cassette including a plurality of second spooley assemblies, each of the plurality of second spooley assemblies including a spool and a pulley and configured to be driven by a corresponding one of the plurality of second drive-side crown elements; and a third cassette including a plurality of third spooley assemblies, each of the plurality of third spooley assemblies including a spool and a pulley and configured to be driven by a corresponding one of the plurality of third drive-side crown elements.

15. The robotic subsystem of claim 14, further comprising:

a first drape plate configured to be disposed between the first drive unit and the first cassette;

a second drape plate configured to be disposed between the second drive unit and the second cassette; and a third drape plate configured to be disposed between the third drive unit and the third cassette.

16. The robotic subsystem of claim 14, wherein the first cassette is a first robotic arm assembly, the second cassette is a second robotic arm assembly, and the third cassette is a camera assembly.

17. The robotic subsystem of claim 16, wherein the first robotic arm assembly, the second robotic arm assembly, and the camera assembly are configured for insertion via a single trocar.

\* \* \* \* \*